US008071559B2

(12) United States Patent
Hannon et al.

(10) Patent No.: US 8,071,559 B2
(45) Date of Patent: Dec. 6, 2011

(54) COMPOSITIONS AND METHODS FOR CANCER DIAGNOSIS AND TREATMENT

(75) Inventors: Gregory J. Hannon, Huntington, NY (US); Scott Hammond, Pittsboro, NC (US); Lin He, Cold Spring Harbor, NY (US); John Michael Thomson, Apex, NC (US); Summer Goodson, Chapel Hill, NC (US)

(73) Assignees: Cold Spring Harbor Laboratory, Cold Spring Harbor, NY (US); University of North Carolina, Chapel Hill, NC (US)

( * ) Notice: Subject to any disclaimer, the term of this patent is extended or adjusted under 35 U.S.C. 154(b) by 0 days.

(21) Appl. No.: 11/416,854

(22) Filed: May 2, 2006

(65) Prior Publication Data

US 2007/0072204 A1    Mar. 29, 2007

Related U.S. Application Data

(60) Provisional application No. 60/677,090, filed on May 2, 2005.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .................... 514/44 A; 536/23.1; 536/24.1; 536/24.5

(58) Field of Classification Search ............. 435/6, 455, 435/91.31; 536/23.1, 24.5; 514/1, 2, 44
See application file for complete search history.

(56) References Cited

U.S. PATENT DOCUMENTS

| | | | |
|---|---|---|---|
| 5,093,246 | A | 3/1992 | Cech et al. |
| 7,232,806 | B2 * | 6/2007 | Tuschl et al. .................... 514/44 |
| 7,759,319 | B2 | 7/2010 | Lollo et al. |
| 2005/0186205 | A1 * | 8/2005 | Anderson et al. .......... 424/144.1 |
| 2005/0261218 | A1 * | 11/2005 | Esau et al. ...................... 514/44 |
| 2008/0268453 | A1 * | 10/2008 | Seto et al. ......................... 435/6 |

FOREIGN PATENT DOCUMENTS

| | | |
|---|---|---|
| WO | WO03/029459 | 4/2003 |
| WO | WO2005/078139 | 8/2005 |

OTHER PUBLICATIONS

Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Branch, A. Trends in Biochem. Sci., vol. 23, pp. 45-50 (1998).*
Crooke, S., Antisense Research & Application, Chapter 1, pp. 1-50. Ed. by S. Crooke, Springer-Verlag, Publ. (1998).*
Opalinska et al, Nature Rev., vol. 1, pp. 503-514 (2002).*
Ota et al., Cancer Research, vol. 64, pp. 3087-3095 (2004).*
Cheng et al., 2005, Antisense inhibition of human miRNAs and indications for an involvement of miRNA in cell growth and apoptosis, Nucleic Acids Res. 33(4):1290-1297.
Couzin, 2002, Breakthrough of the year. Small RNAs make big splash, Science 298(5602):2296-7.
Dennis, 2002, Small RNAs: the genome's guiding hand? Nature 420(6917):732.
Griffiths-Jones, 2004, The microRNA Registry, Nucleic Acids Res. 32:D109-D111.
He and Hannon, 2004, MicroRNAs: Small RNAs with a big role in gene regulation, Nature 5:522-531.
He et al., 2005, A microRNA polycistron as a potential human oncogene, Nature 435(9):828-833.
Hutvágner et al., 2004, Sequence-Specific Inhibition of Small RNA Function, PloS Biology 2(4):465-475.
Kidner and Martienssen, 2003, Macro effects of microRNAs in plants, Trends Genet. 19(1):13-6.
Meister et al., 2004, Sequence-Specific inhibition of microRNA- and siRNA-induced RNA silencing, RNA Journal 10:544-550.
Zeng and Cullen, 2003, Sequence requirements for micro RNA processing and function in human cells, RNA 9(1):112-123.
Eis et al., 2005, Accumulation of miR-155 and *BIC* RNA in human B cell lymphomas, Proc. Natl. Acad. Sci. USA 102(10)3627-3632.
Lagos-Quintana et al., 2001, Identification of Novel Genes Coding for Small Expressed RNAs, Science 294:853-858.
Mourelatos et al., 2002, miRNPs: a novel class of ribonucleoproteins containing numerous microRNAs, Genes & Dev. 16:720-728.
Ota et al., 2004, Identification and Characterization of a Novel Gene, *CI3orf25*, as a Target for 13q31-q32 Amplification in Malignant Lymphoma, Cancer Res. 64:3087-3095.
Bartel et al., "MicroRNA: Genomics, Biogenesis, Mechanism, and function," Cell, vol. 116, pp. 281-297 (Jan. 23, 2004).
Czech et al., "MicroRNAs as therapeutic targets," The new England Journal of Medicine, vol. 354, pp. 1194-1195 (Mar. 16, 2006).
Elmen et al., "LNA-mediated microRNA silencing in non-human primates," Nature, vol. 452, pp. 896-900, (Apr. 17, 2008).
Esau et al., "miR-122 regulation of lipid metabolism revealed by in vivo antisense targeting," Cell metabolism, vol. 3, pp. 87-98 (Feb. 2006). Fluiter et al., "In vivo tumor growth inhibition and bio distribution studies of locked nucleic acid (LNA) antisense oligonucleotides," Nucleic Acids Research, vol. 31, pp. 953-962 (2003).
Krutzfeldt et al., Silencing of microRNAs in vivo with 'antagomirs,' Nature Letters, vol. 438, pp. 685-689, (2005).
Michael et al., "Reduced Accumulation of Specific MicroRNAs in colorectal Neoplasia," Molecular Cancer Research, vol. 1, pp. 882-891 (Oct. 2003).
Morrissey et al., "Potent and persistent in vivo anti-HBV activity of chemically modified siRNAs," Nature biotechnology, vol. 23, pp. 1002-1007 (Aug. 2005).
Obad et al., "Silencing of microRNA families by seed-targeting tiny LNAs. Supplementary Information" Nature Genetics, vol. 43. pp. 1-20 (2011).
Obad et al., "Silencing of microRNA families by seed-targeting tiny LNAs." Nature Genetics, vol. 43. pp. 371-378 (2011).
Soutschek et al., "Therapeutic silencing of an endogenous gene by Systemic administration of modified siRNAs," Nature, vol. 432, pp. 173-178 (Nov. 2004).
Zimmermann et asl., "RNAi-mediated gene silencing in non-human primates",Nature, vol. 441, pp. 111-114, (May 4, 2006).

* cited by examiner

*Primary Examiner* — Sean McGarry
(74) *Attorney, Agent, or Firm* — Wilmer Cutler Pickering Hale and Dorr LLP

(57) ABSTRACT

The application relates to methods and compositions for the diagnosis, prevention, and treatment of tumors and cancers in mammals, for example, humans, utilizing the mir17-92 cluster. The application further relates to screening methods to identify compounds and reagents useful in cancer diagnosis, prevention, and therapy.

24 Claims, 11 Drawing Sheets

Figure 1:
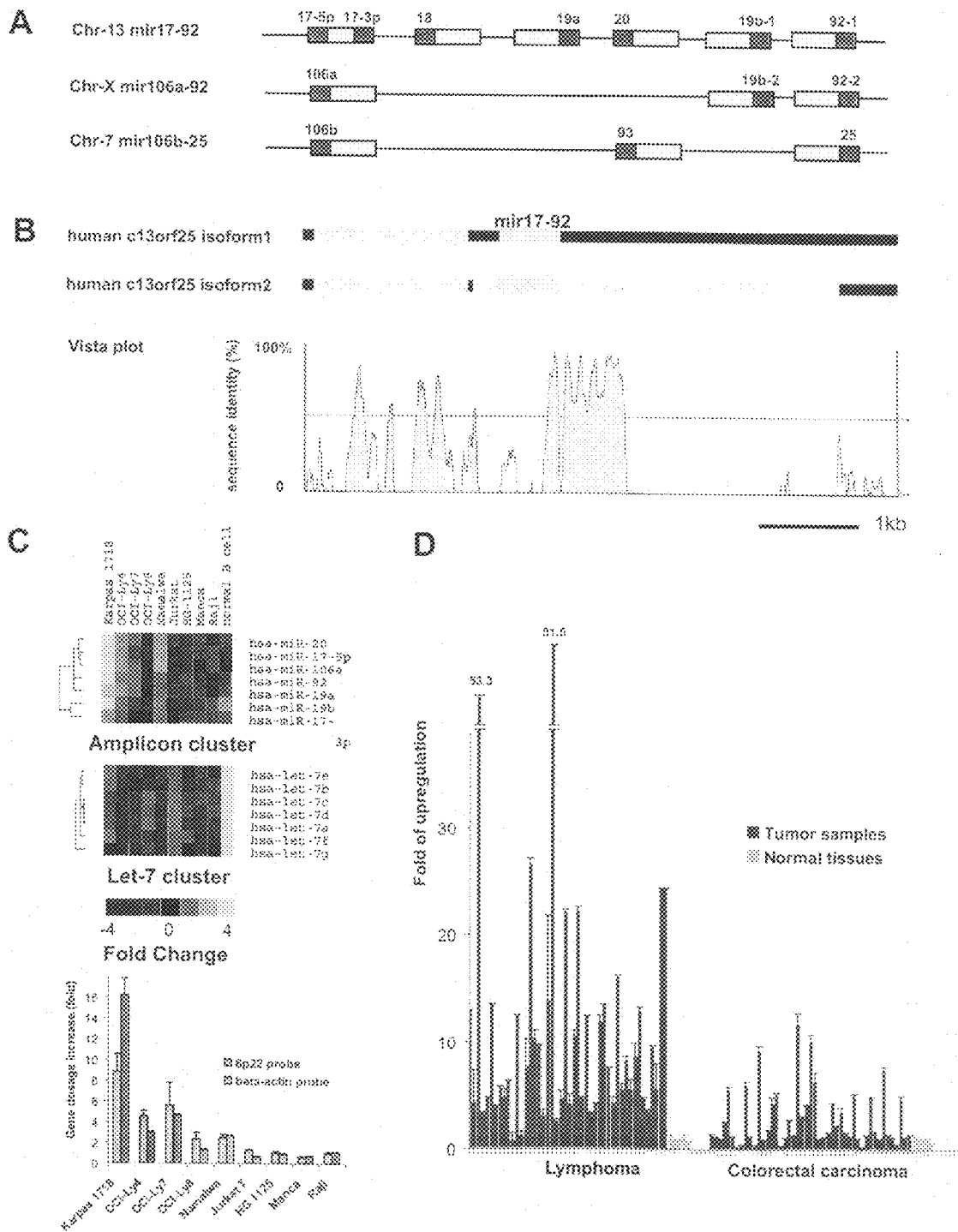

(9 of 11 Drawing Sheet(s) Filed in Color)

Figure 3
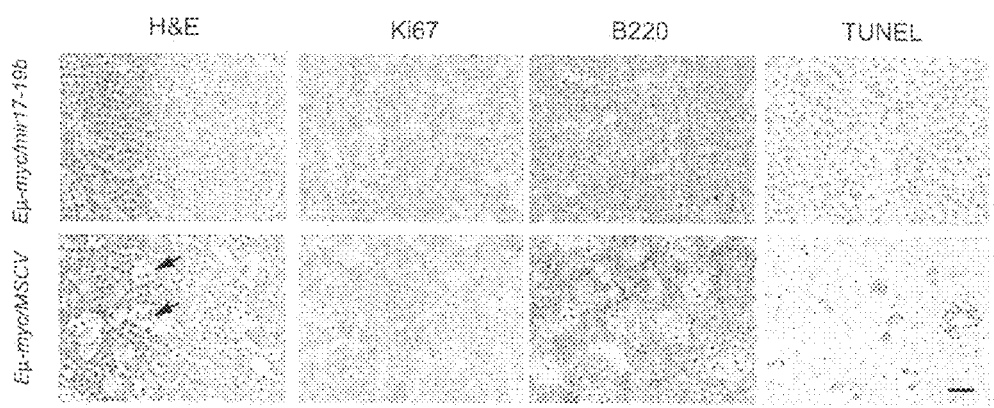
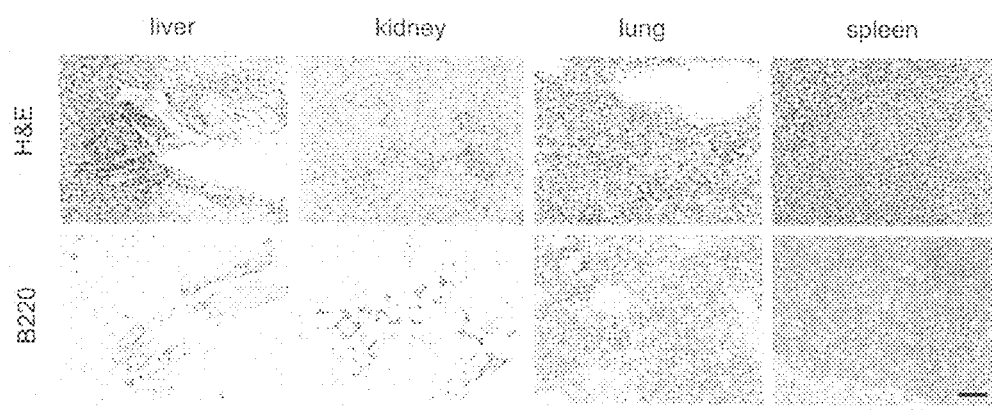
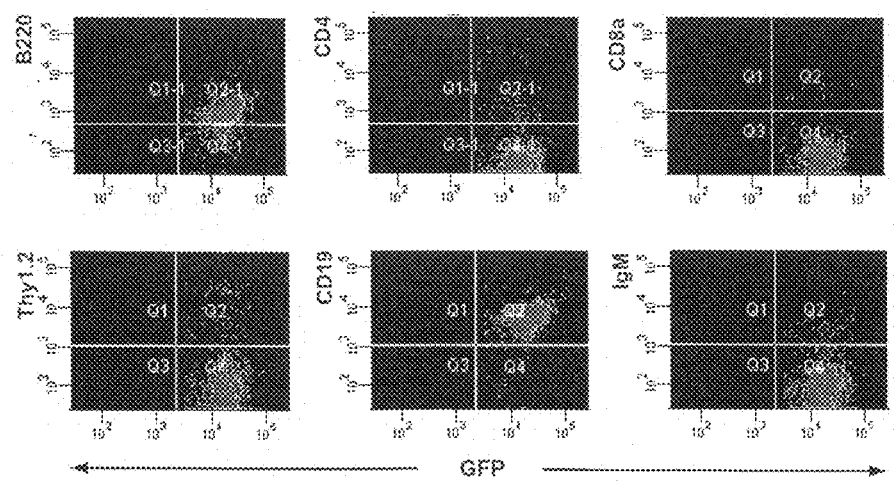

| Genotype | immunophenotyping | # of animals |
|---|---|---|
| Eu-myc, 17-19b (n=9) | B220$^+$, Thy1$^{-/low}$, IgM$^-$, CD19$^+$, CD4$^-$, CD8$^-$ | 7 |
| | B220$^+$, Thy1$^{-/low}$, IgM$^+$, CD19$^+$, CD4$^-$, CD8$^-$ | 0 |
| | B220$^+$, Thy1$^{-/low}$, IgM$^-$&IgM$^+$, CD19$^+$, CD4$^-$, CD8$^-$ | 1 |
| Eu-myc, 19b (n=9) | B220$^+$, Thy1$^{-/low}$, IgM$^-$, CD19$^+$, CD4$^-$, CD8$^-$ | 6 |
| | B220$^+$, Thy1$^{-/low}$, IgM$^+$, CD19$^+$, CD4$^-$, CD8$^-$ | 3 |
| | B220$^+$, Thy1$^{-/low}$, IgM$^-$&IgM$^+$, CD19$^+$, CD4$^-$, CD8$^-$ | 0 |
| Eu-myc, 19a-19b (n=6) | B220$^+$, Thy1$^{-/low}$, IgM$^-$, CD19$^+$, CD4$^-$, CD8$^-$ | 5 |
| | B220$^+$, Thy1$^{-/low}$, IgM$^+$, CD19$^+$, CD4$^-$, CD8$^-$ | 1 |
| | B220$^+$, Thy1$^{-/low}$, IgM$^-$&IgM$^+$, CD19$^+$, CD4$^-$, CD8$^-$ | 0 |
| Eu-myc, 18 (n=4) | B220$^+$, Thy1$^{-/low}$, IgM$^-$, CD19$^+$, CD4$^-$, CD8$^-$ | 2 |
| | B220$^+$, Thy1$^{-/low}$, IgM$^+$, CD19$^+$, CD4$^-$, CD8$^-$ | 1 |
| | B220$^+$, Thy1$^{-/low}$, IgM$^-$&IgM$^+$, CD19$^+$, CD4$^-$, CD8$^-$ | 1 |

FIGURE 9 ttgaggtgttaattctaattatctatttcaaatttagcaggaaaaaagagaacatcaccttgtaaaactga
agattgtgaccaGTCAGAATAATGTCAAAGTGCTTACAGTGCAGGTAGTGATATGTGCATCTACTGCAGTG
AAGGCACTTGTAGCATTATGGTGACagctgcctcgggaagccaagttgggctttaaagtgcagggcctgct
gatgttgagtgcttttTGTTCTAAGGTGCATCTAGTGCAGATAGTGAAGTAGATTAGCATCTACTGCCCTA
AGTGCTCCTTCTGGCAtaagaagttatgtattcatccaataattcaagccaagcaagtatataggtgtttt
aatagttttgtttGCAGTCCTCTGTTAGTTTTGCATAGTTGCACTACAAGAAGAATGTAGTTGTGCAAAT
CTATGCAAAACTGATGGTGGCCTGCtatttccttcaaatgaatgatttttactaattttgtgtactttat
tgtgtcgatgtagaatctgcctggtctatctgatgtgacagcttctGTAGCACTAAAGTGCTTATAGTGCA
GGTAGTGTTTAGTTATCTACTGCATTATGAGCACTTAAAGTACTGCtagctgtagaactccagcttcggcc
tgtcgcccaatcaaactgtcctgttactgaaCACTGTTCTATGGTTAGTTTTGCAGGTTTGCATCCAGCTG
TGTGATATTCTGCTGTGCAAATCCATGCAAAACTGACTGTGGTAGTGaaaagtctgtagaaaagtaaggga
aactcaaacccCTTTCTACACAGGTTGGGATCGGTTGCAATGCTGTGTTTCTGTATGGTATTGCACTTGTC
CCGGCCTGTTGAGTTTGGtggggattgtgaccagaagattttgaaaattaaatattactgaagatttcgac
ttccactgttaaatgtacaagatacat

FIGURE 11

SEQUENCE LISTING

<160> NUMBER OF SEQ ID NOS: 12

<210> SEQ ID NO 1
<211> LENGTH: 950
<212> TYPE: DNA
<213> ORGANISM: Homo sapiens

<400> SEQUENCE: 1

```
ttgaggtgtt aattctaatt atctatttca aatttagcag gaaaaaagag aacatcacct      60
tgtaaaactg aagattgtga ccagtcagaa taatgtcaaa gtgcttacag tgcaggtagt     120
gatatgtgca tctactgcag tgaaggcact tgtagcatta tggtgacagc tgcctcggga     180
agccaagttg ggctttaaag tgcagggcct gctgatgttg agtgcttttt gttctaaggt     240
```

-continued

| | | |
|---|---|---|
| gcatctagtg cagatagtga agtagattag catctactgc cctaagtgct ccttctggca | 300 | |
| taagaagtta tgtattcatc caataattca agccaagcaa gtatataggt gttttaatag | 360 | |
| tttttgtttg cagtcctctg ttagttttgc atagttgcac tacaagaaga atgtagttgt | 420 | |
| gcaaatctat gcaaaactga tggtggcctg ctatttcctt caaatgaatg attttttacta | 480 | |
| attttgtgta cttttattgt gtcgatgtag aatctgcctg gtctatctga tgtgacagct | 540 | |
| tctgtagcac taaagtgctt atagtgcagg tagtgtttag ttatctactg cattatgagc | 600 | |
| acttaaagta ctgctagctg tagaactcca gcttcggcct gtcgcccaat caaactgtcc | 660 | |
| tgttactgaa cactgttcta tggttagttt tgcaggtttg catccagctg tgtgatattc | 720 | |
| tgctgtgcaa atccatgcaa aactgactgt ggtagtgaaa agtctgtaga aaagtaaggg | 780 | |
| aaactcaaac ccctttctac acaggttggg atcggttgca atgctgtgtt tctgtatggt | 840 | |
| attgcacttg tcccggcctg ttgagtttgg tggggattgt gaccagaaga ttttgaaaat | 900 | |
| taaatattac tgaagatttc gacttccact gttaaatgta caagatacat | 950 | |

<210> SEQ ID NO 2
<211> LENGTH: 27
<212> TYPE: DNA
<213> ORGANISM: Homo sapiens

<400> SEQUENCE: 2
cagtaaaggt aaggagagct caatctg                27

<210> SEQ ID NO 3
<211> LENGTH: 31
<212> TYPE: DNA
<213> ORGANISM: Homo sapiens

<400> SEQUENCE: 3
catacaacca ctaagctaaa gaataatctg a            31

<210> SEQ ID NO 4
<211> LENGTH: 31
<212> TYPE: DNA
<213> ORGANISM: Homo sapiens

<400> SEQUENCE: 4
tggaaataag atcatcatgc ccacttgaga c            31

<210> SEQ ID NO 5
<211> LENGTH: 21
<212> TYPE: DNA
<213> ORGANISM: Homo sapiens

<400> SEQUENCE: 5
gcaaagacct gtacgccaac a                      21

<210> SEQ ID NO 6
<211> LENGTH: 18
<212> TYPE: DNA
<213> ORGANISM: Homo sapiens

<400> SEQUENCE: 6
tgcatcctgt cggcaatg                          18

<210> SEQ ID NO 7
<211> LENGTH: 20
<212> TYPE: DNA
<213> ORGANISM: Homo sapiens

```
<400> SEQUENCE: 7
tggcggcacc accatgtacc                                                   20

<210> SEQ ID NO 8
<211> LENGTH: 24
<212> TYPE: DNA
<213> ORGANISM: Homo sapiens

<400> SEQUENCE: 8
ggtctctatt tgcacttggc tgat                                              24

<210> SEQ ID NO 9
<211> LENGTH: 25
<212> TYPE: DNA
<213> ORGANISM: Homo sapiens

<400> SEQUENCE: 9
ttttcattgt tgaccaagct agaca                                             25

<210> SEQ ID NO 10
<211> LENGTH: 29
<212> TYPE: DNA
<213> ORGANISM: Homo sapiens

<400> SEQUENCE: 10
tagggcatac tgcctgcata tttcctgct                                         29

<210> SEQ ID NO 11
<211> LENGTH: 23
<212> TYPE: RNA
<213> ORGANISM: Artificial Sequence
<220> FEATURE:
<223> OTHER INFORMATION: antisense oligonucleotide

<400> SEQUENCE: 11
ucaguuuugc auggauuugc aca                                               23

<210> SEQ ID NO 12
<211> LENGTH: 22
<212> TYPE: RNA
<213> ORGANISM: Artificial Sequence
<220> FEATURE:
<223> OTHER INFORMATION: antisense oligonucleotide

<400> SEQUENCE: 12
uaucugcacu agaugcaccu ua                                                22
```

US 8,071,559 B2

COMPOSITIONS AND METHODS FOR CANCER DIAGNOSIS AND TREATMENT

RELATED APPLICATIONS

This Application claims the benefit of U.S. Provisional Application No. 60/677,090, filed May 2, 2005, which application is hereby incorporated by reference in its entirety.

BACKGROUND

Cancer is a major cause of morbidity in the United States. For example, in 1996, the American Cancer Society estimated that 1,359,150 people were diagnosed with a malignant neoplasm and 554,740 died from one of these diseases. Cancer is responsible for 23.9 percent of all American deaths and is exceeded only by heart disease as a cause of mortality (33 percent). Unfortunately, cancer mortality is increasing and sometime early in this century, cancer is expected to become the leading cause of mortality in the United States as it already is in Japan.

Cancers share the characteristics of disordered control over normal cell division, growth, and differentiation. Their initial clinical manifestations are extremely heterogeneous, with over 70 types of cancer arising in virtually every organ and tissue of the body. Moreover, some of those similarly classified cancer types may represent multiple different molecular diseases. Unfortunately, some cancers may be virtually asymptomatic until late in the disease course, when treatment is more difficult, and prognosis grim.

Treatment for cancer typically includes surgery, chemotherapy, and/or radiation therapy. Although nearly 50 percent of cancer patients can be effectively treated using these methods, the current therapies all induce serious side effects which diminish quality of life. The identification of novel therapeutic targets and diagnostic markers is desirable for improving the diagnosis, prognosis, and treatment of cancer patients. Such novel therapeutic targets and diagnostic markers are provided herein.

SUMMARY OF THE INVENTION

One aspect of the present invention provides a method for diagnosing a cancer in a mammal, comprising: a) determining the copy number of the mir17-92 cistron in a biological sample from a region of the mammal that is suspected to be precancerous or cancerous, thereby generating data for a test gene copy number; and b) comparing the test gene copy number to data for a control gene copy number, wherein an amplification of the gene in the biological sample relative to the control indicates the presence of a precancerous lesion or a cancer in the mammal.

Another aspect of the present invention provides a method for diagnosing a cancer in a mammal, comprising: a) determining the level of expression of one or more of the miRNAs encoded by the mir17-92 cistron in a biological sample from a region of the mammal that is suspected to be precancerous or cancerous, thereby generating data for a test level; and b) comparing the test level to data for a control level for each miRNA encoded by the mir17-92 cistron, wherein an elevated test level of the biological sample relative to the control level for at least one member of the mir17-92 cistron indicates the presence of a precancerous lesion or a cancer in the mammal.

A further aspect of the present invention provides a method of identifying an inhibitor of the mir17-92 cistron comprising: a) contacting a candidate agent with a cancer cell expressing one or more miRNAs encoded by the mir17-92 cistron; b) determining the expression level of one or more miRNAs encoded by the mir17-92 cistron in the cell, thereby generating data for a test level; and c) comparing the test level of each miRNA encoded by the mir17-92 cistron to the respective level in the cancer cell prior to contacting the candidate agent, wherein a decrease in the level of one or more miRNAs in the test level indicates that the candidate agent is an inhibitor of the mir17-92 cistron.

Another aspect of the present invention provides a method of identifying an inhibitor of mir17-19b comprising: a) contacting a candidate agent with a cancer cell expressing one or more miRNAs encoded by mir17-19b, the truncated mir17-92 cistron; b) determining the expression level of one or more miRNAs encoded by the mir17-19b in the cell, thereby generating data for a test level; and c) comparing the test level of each miRNA encoded by mir17-19b to the respective level in the cancer cell prior to contacting the candidate agent, wherein a decrease in the level of one or more miRNAs in the test level indicates that the candidate agent is an inhibitor of mir17-19b.

Another aspect of the present invention provides a method of identifying an inhibitor of the mir17-92 cistron comprising: a) contacting a candidate agent with a cancer cell expressing one or more miRNAs encoded by the mir17-92 cistron; b) determining the activity of one or more miRNAs encoded by the mir17-92 cistron in the cell, thereby generating data for a test activity level; and c) comparing the test activity level of each miRNA encoded by the mir17-92 cistron to the respective activity level in the cancer cell prior to contacting the candidate agent, wherein a decrease in the test activity level of one or more miRNAs encoded by the mir17-92 cistron indicates that the candidate agent is an inhibitor of the mir17-92 cistron.

Another aspect of the present invention provides a method of identifying a mir17-19b inhibitor comprising: a) contacting a candidate agent with a cancer cell expressing one or more miRNAs encoded by mir17-19b; b) determining the activity of one or more miRNAs encoded by mir17-19b in the cell, thereby generating data for a test activity level; and c) comparing the test activity level of each miRNA encoded by mir17-19b to the respective activity level in the cancer cell prior to contacting the candidate agent, wherein a decrease in the test activity level of one or more miRNAs encoded by mir17-19b indicates that the candidate agent is a mir17-19b inhibitor.

Another aspect of the present invention provides a method for determining the efficacy of a therapeutic treatment regimen in a patient, comprising: a) measuring the expression level of one or more miRNAs encoded by the mir17-92 cistron in a first biological sample obtained from the patient, thereby generating data for a control level; b) administering the treatment regimen to the patient; c) measuring the expression level of at least one or more miRNA encoded by the mir17-92 cistron in a second biological sample from the patient at a time following administration of the treatment regimen, thereby generating data for a test level; and d) comparing the control level to the test level on a miRNA-by-miRNA basis, wherein data showing no decrease for any miRNA of the mir17-92 cistron in the test level relative to the control level indicates that the treatment regimen is not effective in the patient.

Another aspect of the present invention provides a method for determining the efficacy of a therapeutic treatment regimen in a patient, comprising: a) measuring the expression level of one or more miRNAs encoded by mir17-19b in a first biological sample obtained from the patient, thereby generating data for a control level; b) administering the treatment regimen to the patient; c) measuring the expression level of at least one or more miRNA encoded by mir17-19b in a second biological sample from the patient at a time following administration of the treatment regimen, thereby generating data for a test level; and d) comparing the control level to the test level on a miRNA-by-miRNA basis, wherein data showing no decrease for any miRNA of mir17-19b in the test level relative to the control level indicates that the treatment regimen is not effective in the patient.

Still a further aspect of the present invention provides a method for selecting candidate agent having a therapeutic effect in a patient, comprising: a) measuring the expression level of one or more miRNAs encoded by the mir17-92 cistron in a first biological sample obtained from the patient, thereby generating data for a control level; b) administering the candidate agent to the patient; c) measuring the expression level of one or more miRNA encoded by the mir17-92 cistron in a second biological sample from the patient at a time following administration of the test molecule, thereby generating data for a test level; d) comparing the control level to the test level on a miRNA-by-miRNA basis, wherein data showing no decrease for any miRNA of the mir17-92 cistron, in the test level relative to the control level indicates that the candidate agent is not effective in the patient; and e) eliminating the candidate agent from further evaluation or study.

Another aspect of the present invention provides a method for eliminating a candidate agent lacking a therapeutic effect in a patient, comprising: a) measuring the expression level of one or more miRNAs encoded by the mir17-92 cistron in a first biological sample obtained from the patient, thereby generating data for a control level; b) administering the candidate agent to the patient; c) measuring the expression level of one or more miRNA encoded by the mir17-92 cistron in a second biological sample from the patient at a time following administration of the test molecule, thereby generating data for a test level; d) comparing the control level to the test level on a miRNA-by-miRNA basis, wherein data showing no decrease for any miRNA of the mir17-92 cistron, in the test level relative to the control level indicates that the candidate agent is not effective in the patient; and e) eliminating the candidate agent from further evaluation or study.

Another aspect of the present invention provides a method for treating or preventing cancer in an individual in need thereof, comprising administering to the individual an effective amount of a mir17-92 cistron inhibitor.

Another aspect of the present invention provides a method for treating or preventing cancer in an individual in need thereof, comprising administering to the individual an effective amount of a mir17-19b inhibitor.

In another aspect, the invention provides an isolated nucleic acid compound comprising a sequence that hybridizes to a mir17-92 cistron transcript, or mir17-19b transcript, under physiological conditions and decreases the expression or activity of at least one miRNA encoded by the mir17-92 cistron, or mir17-19b cistron, in a cell. In certain embodiments, the isolated nucleic acid compound hybridizes to a transcript encoded by SEQ ID NO: 1, or a portion thereof, such as, for example, a portion comprising at least 10 contiguous nucleotide residues of SEQ ID NO: 1. In exemplary embodiments, the isolated nucleic acid compound hybridizes to a portion of SEQ ID NO: 1 comprising nucleotide residues 84-167, 230-300, 235-256, 370-451, 544-614, 671-757, 793-870, 235-256, or 724-746 or SEQ ID NO: 1. In certain embodiments, the nucleic acid compound is from about 14 to about 50 nucleotides in length. In certain embodiments, the nucleic acid compound hybridizes to at least 8 contiguous nucleotides of a transcript encoded by the mir17-92 cistron. In certain embodiments, the nucleic acid compound is single-stranded. In certain embodiments, the nucleic acid compound is double-stranded. In certain embodiments, the nucleic acid compound is a DNA molecule, optionally comprising one or more modified backbone or base moieties. In certain embodiments, the nucleic acid compound is a RNA molecule, optionally comprising one or more modified backbone or base moieties. In certain embodiments, the nucleic acid compound comprises a DNA strand and a RNA strand and optionally comprises one or more modified backbone or base moieties.

In certain embodiments, the nucleic acid compound is an antisense nucleic acid compound. In certain embodiments, the antisense nucleic acid compound is from about 15 to about 30 nucleotides in length. In certain embodiments, the antisense nucleic acid compound comprises SEQ ID NO: 11. In certain embodiments, the antisense nucleic acid compound comprises SEQ ID NO: 12. In certain embodiments, the antisense nucleic acid compound comprises one or modified backbone or base moieties. In certain embodiments, the antisense nucleic acid compound has at least one internucleotide linkage selected from the group consisting of alkylphosphonates, phosphorothioates, phosphorodithioates, alkylphosphonothioates, phosphoramidates, phosphate esters, carbamates, acetamidate, carboxylmethyl esters, carbonates, and phosphate triesters. In certain embodiments, the modified antisense nucleic acid comprises at least one 2'-O-alkylated ribonucleotide.

In certain embodiments, the nucleic acid compound is an RNAi construct. In certain embodiments, the RNAi construct is a dsRNA, optionally comprising one or more modified backbone or base moieties. In certain embodiments, the RNAi construct is a hairpin RNA, optionally comprising one or more modified backbone or base moieties. In certain embodiments, the duplex portion of the RNAi construct is from about 21 to about 23 nucleotides in length. In certain embodiments, the RNAi construct comprises one or more backbone or base moieties. In certain embodiments, the modified RNAi construct has at least one internucleotide linkage selected from the group consisting of alkylphosphonates, phosphorothioates, phosphorodithioates, alkylphosphonothioates, phosphoramidates, phosphate esters, carbamates, acetamidate, carboxylmethyl esters, carbonates, and phosphate triesters. In certain embodiments, the modified RNAi construct comprises at least one 2'-O-alkylated ribonucleotide.

In certain embodiments, the nucleic acid compound is an enzymatic nucleic acid. In certain embodiments, the enzymatic nucleic acid is a ribozyme. In certain embodiments, the enzymatic nucleic acid is a DNA enzyme.

In another aspect, the invention provides a nucleic acid compound that inhibits the expression in a cell of at least one miRNA encoded by the mir17-92 cistron, or mir17-19b cistron, by at least 50%. In certain embodiments, the nucleic acid compound inhibits the expression in a cell of at least one miRNA encoded by the mir17-92 cistron, or mir17-19b cistron, by at least 5-fold.

In another aspect, the invention provides a pharmaceutical composition comprising a nucleic acid compound and a pharmaceutically acceptable carrier, wherein the nucleic acid compound hybridizes to a mir17-92 cistron transcript under physiological conditions and decreases the expression or activity of at least one miRNA encoded by the mir17-92 cistron in a cell. In certain embodiments, the pharmaceutical composition comprises a nucleic acid compound selected from the group consisting of: an RNAi construct and an antisense nucleic acid compound.

In another aspect, the invention provides a method of inhibiting expression or activity of at least one miRNA encoded by a mir17-92 cistron in a cell, comprising contacting the cell with an effective amount of the nucleic acid compound described herein. In certain embodiments, the nucleic acid compound is selected from the group consisting of: an RNAi construct and an antisense nucleic acid compound.

In another aspect, the invention provides a method of inhibiting mir17-92 cistron expression in a cell, comprising contacting the cell with an effective amount of a nucleic acid compound described herein. In certain embodiments, the nucleic acid compound is selected from the group consisting of: an RNAi construct and an antisense nucleic acid compound.

It is contemplated that all embodiments described above are applicable to all aspects of the invention. It is also contemplated that any of the above embodiments can be freely combined with one or more other such embodiments whenever appropriate.

Specific embodiments of the invention are described in more detail below. However, these are illustrative embodiments, and should not be construed as limiting in any respect.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 1: The mir17-92b cluster shows increased expression in B-cell lymphoma samples and cell lines. A. Genomic organization of three polycistronic miRNA clusters is shown. There are five paralog groups located in the three homologous clusters with a conserved order, miR-17/miR-106a/miR-106b, miR-18, miR-19a/miR-19b-1/miR-19b-2, miR-20/93, and miR-92-1/miR-92-2/miR-25 (yellow boxes, pre-miRNAs; purple boxes, mature miRNAs). B. The level of conservation between human and mouse homologs is represented using mVista plot[27] (dark blue, exons; light blue, introns; orange, the mir17-92 cluster). Two alternative isoforms have been detected for the human gene and these are shown schematically. C. MicroRNA expression levels in cell lines carrying the 13q31-q32 amplicon, including Karpas 1718, OCI-Ly4, and OCI-Ly7, were compared to those in leukemia and lymphoma cell lines lacking this genetic lesion and to normal B-cells isolated from cortical blood (upper panel). We included in this analysis the OCI-Ly8 cell line, which was previously implicated as a cell line carrying the 13q3132 amplicon, yet exhibited no gene dosage increase at the c13orf25 locus in our study. Normalized one-channel measurements for 191 human miRNAs were hierarchically clustered for all miRNA genes represented on the array. An excerpt of the data is shown with the full cluster analysis presented in FIG. 4. The expression map node that correlates with the amplification is shown. The let-7 node is also shown for comparison. (center panel). In the cell lines examined, the expression level of the mir17-92 polycistron correlates with the copy number at the mir17-92 locus (lower panel). D. The level of mir17-92 pri-miRNA was determined by RT-QPCR in 46 lymphomas and 47 colorectal carcinomas, and compared to levels found in corresponding normal tissues from 5 individuals, respectively. For panels C and D, error bars indicate standard deviation from the mean.

Figure 2:
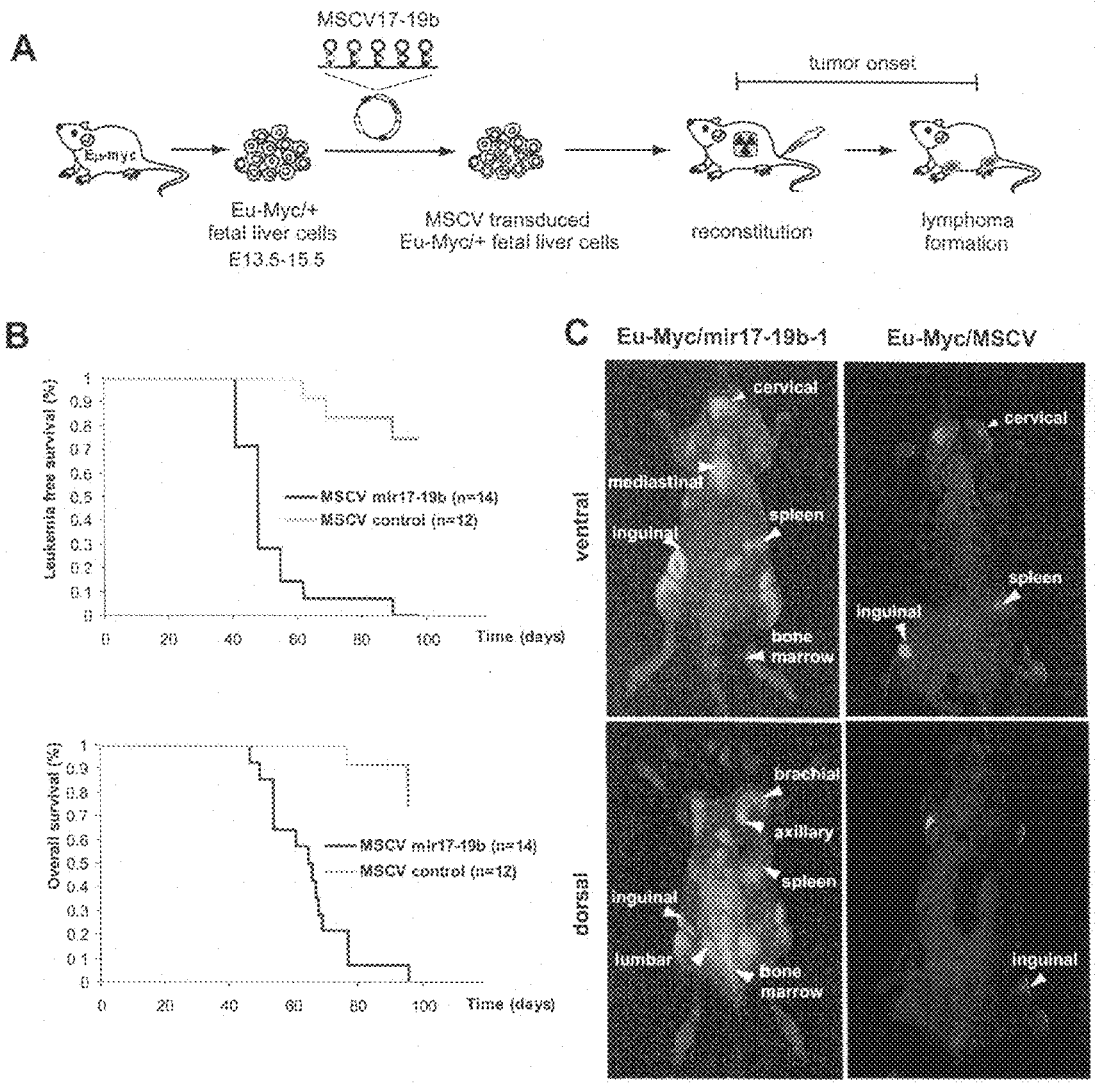

FIG. 2: Overexpression of the mir17-19b cluster accelerates c-myc induced lymphomagenesis in mice. A. Schematic representation of the adoptive transfer protocol using Eμ-myc HSCs. B. Mice reconstituted with HSCs expressing the mir17-19b in an MSCV retroviral vector (MSCV mir17-19b) or infected with a control MSCV virus were monitored by blood smear analysis starting from 5 weeks post transplantation. The Kaplan-Meier curves represent percentage of leukemia-free survival or overall survival as indicated. C. External GFP imaging of tumor bearing mice with Eμ-myc/mir17-19b or Eμ-myc/MSCV shows the overall distribution of tumor cells. Eμ-myc/mir17-19b tumors exhibit a more disseminated phenotype as compared to control tumors. These animals are representative for their genotype following diagnosis.

FIG. 3: Pathological and immunological analysis of lymphomas produced by cooperation between mir17-19b and c-myc. A. H&E, Ki67, B220, and TUNEL staining of Eμ-myc/mir17-19b lymph node tumors. The "starry sky" morphology is a hallmark of cell clusters undergoing apoptosis (black arrows). Scale bar is 10 um. B. H&E and B220 staining of visceral organs, liver, spleen, lung and kidney, showed invasion by Eμ-myc/mir17-19b tumor cells. Invasion was observed both perivascularly and parenchymally in liver. Scale bar is 50 um. C. Immunophenotyping of Eμ-myc/mir17-19b lymphomas. Tumor cells stained positively for the B cell specific marker, B220, but not for T-cell specific markers, CD4, CD8a, and Thy1.2. Tumor cells bore cellular characteristics of pre-B cells, staining positively for CD19 but not for a mature B-cell marker, IgM.

Figure 4:
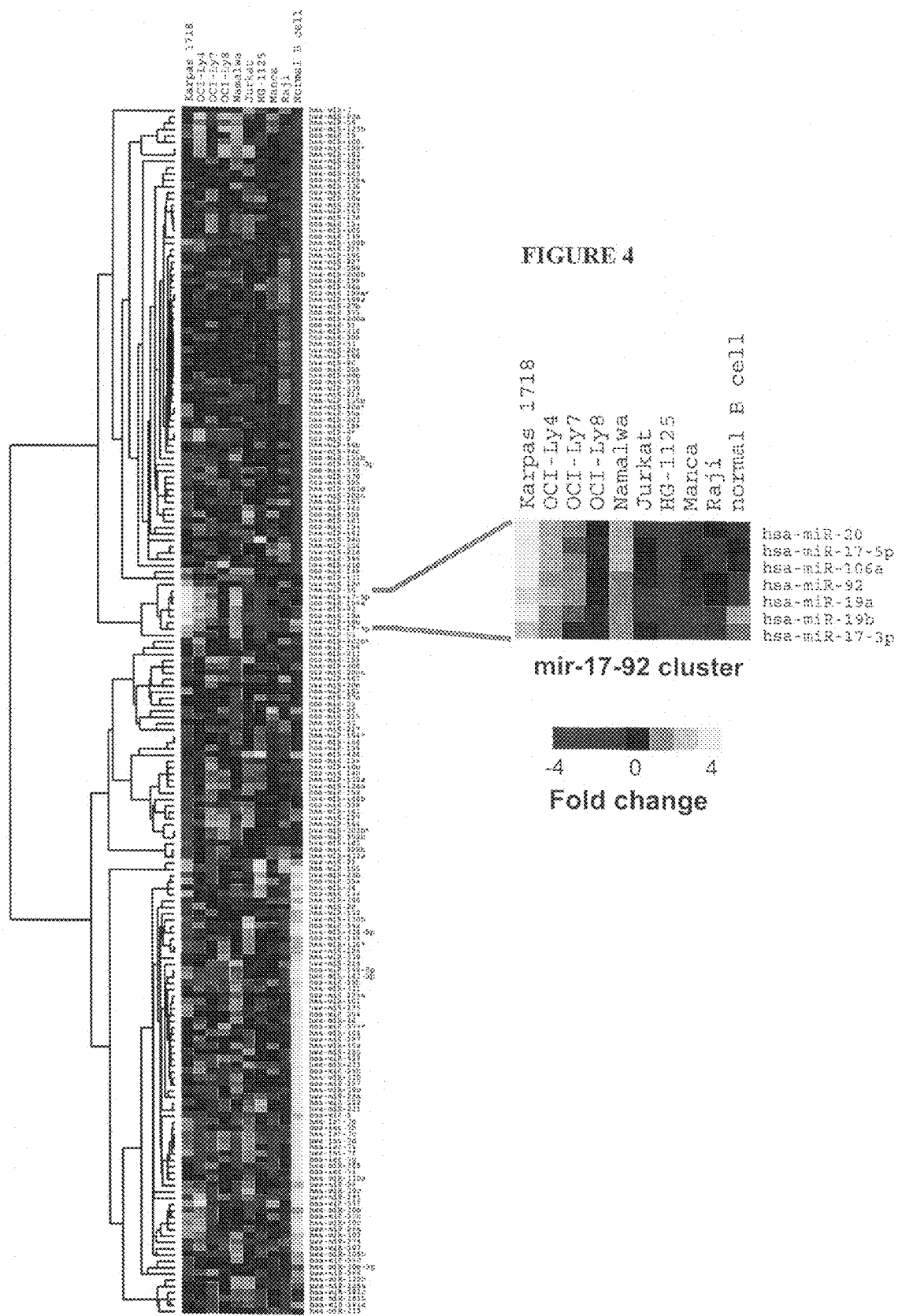

FIG. 4: MicroRNA expression map of leukemia and lymphoma cell lines. MicroRNA expression levels in cell lines previously described to carry the 13q31-q32 amplicon, including Karpas 1718, OCI-Ly4, OCI-Ly7 and OCI-Ly8, were compared to those in leukemia and lymphoma cell lines lacking this genetic lesion and to normal B-cells isolated from cortical blood. Total RNA was labeled with Cy3 and hybridized to microarrays that contain probes to 191 human mature microRNAs. Background subtracted one-channel measurements were log transformed (base 2) and median center normalized. Four independent data sets for each cell line were collapsed by median, and hierarchically clustered by gene only. Yellow indicates high expression relative to the median and blue indicates low expression. The node that corresponds to the mir17-92 locus is expanded on the right.

Figure 5:
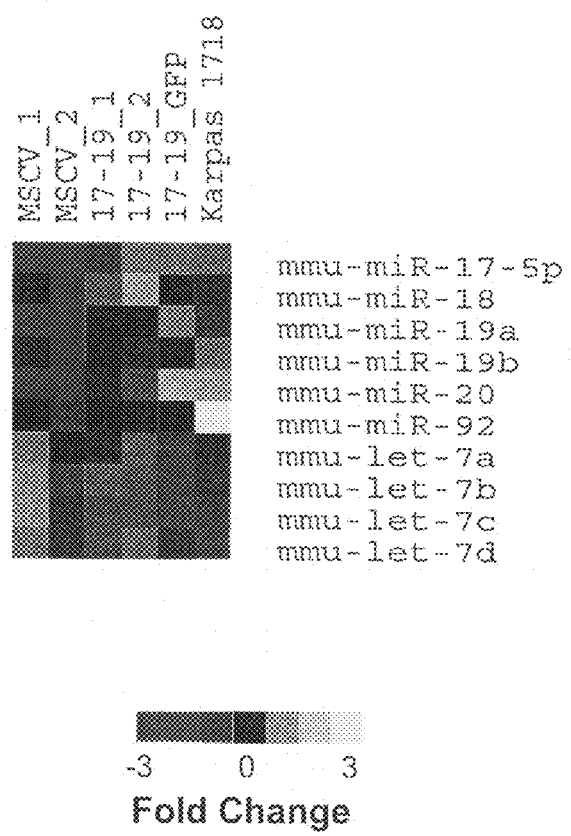

FIG. 5: Ectopic expression of mir17-92 in Eμ-myc/mir17-19b B-cell lymphomas. MicroRNA expression form tow control Eμ-myc/MSCV lymphomas (MSCV__1, MSCV__2) and two Eμ-myc/mir17-19b lymphomas (17-19__1, 17-19__2) was quantitated by microarray analysis. Also measured were microRNA expression levels for Eμ-myc/mir17-19b lymphoma cells that were purified by FACS sorting for linked GFP expression (17-19_GFP). Total RNA was labeled with Cy3 and hybridized to microarrays that contain probes to 198 mouse mature microRNAs. Background subtracted one-channel measurements were log transformed (base 2) and median center normalized. Four independent data sets for each cell line were collapsed by median, except for 17-19__2 lymphoma, which had two data sets only. Karpas 1718, the cell line with the highest 13Q31 amplification, is shown for comparison. The hear map indicates expression of each conserved (mouse/human) microRNA in the mir17-92 locus, with four let-7 microRNAs shown for comparison. Yellow indicates high expression relative to the median and blue indicates low expression.

Figure 6:
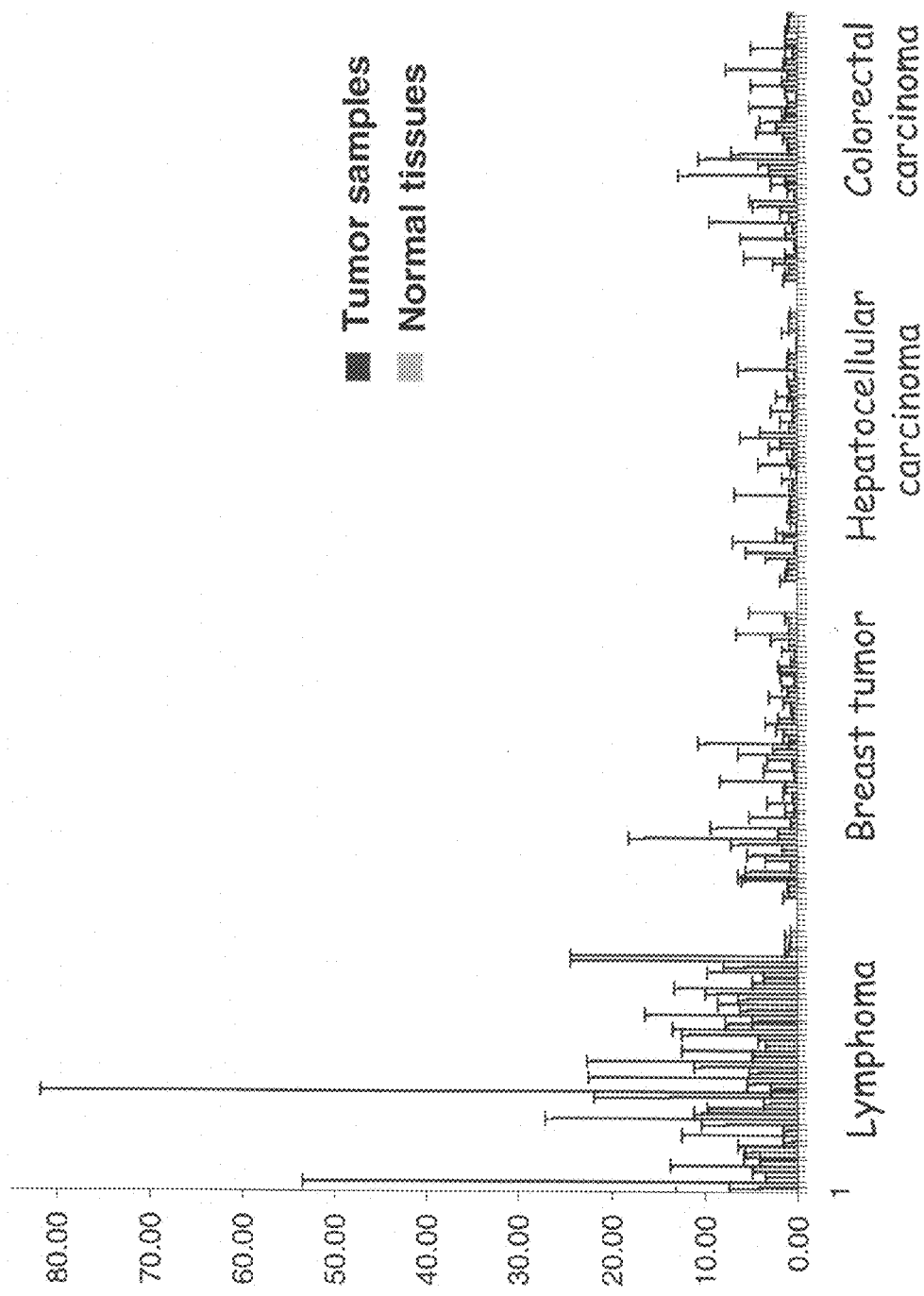

FIG. 6: The level of mir17-92 pri-miRNA was determined by RT-QPCR in lymphomas, breast tumors, hepatocellular carcinoma and colorectal carcinomas, and compared to levels found in corresponding normal tissues, respectively. Error bars indicate standard deviation from the mean.

Figure 7:
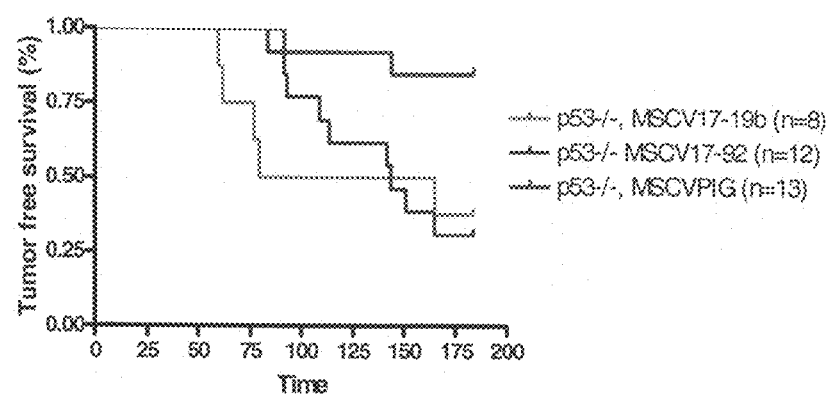

FIG. 7: Oncogenic cooperation between mir17-92 and p53 loss. Over-expression of either mir17-92 or mir17-19b accelerates lymphomagenesis in cooperation with p53 loss. p53$^{-/-}$ mice reconstituted with HSCs expressing mir17-92 (MSCV mir17-92) or mir17-19b (MSCV mir17-19b) in an MSCV retroviral vector or infected with a control MSCV virus (MSCVPIG) were monitored by blood smear analysis. The Kaplan-Meier curves represent percentage of leukemia-free survival or overall survival as indicated. Time is shown in days.

Figure 8:
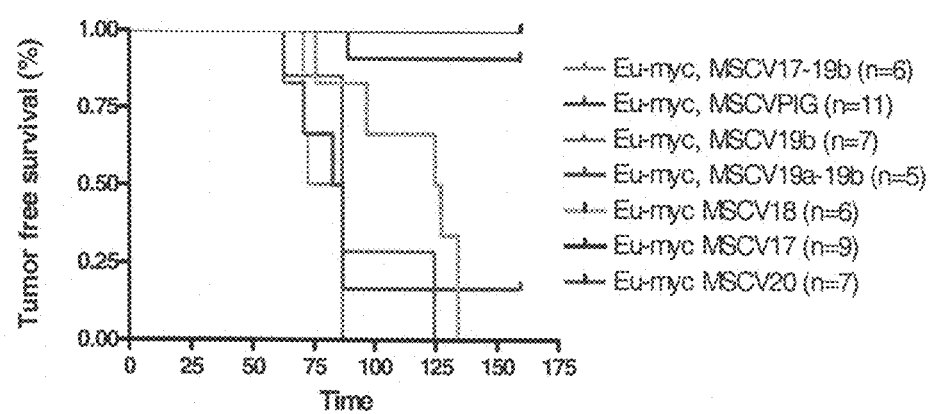

FIG. 8: Overexpression of the individual miRNAs from the mir17-92 polycistron accelerates c-myc induced lymphomagenesis in mice. c-myc cooperates with mir-19b, and to a lesser degree, with mir-18. Measurement of tumor free-survival in mice reconstituted with Eµ-myc/+ HSCs containing miRNAs from the mir17-92 cluster. Mice reconstituted with HSCs expressing the mir17-19b cistron (MSCV17-19b), individual miRNAs mir-17 (MSCV17), mir-18 (MSCV18), mir-19b (MSCV19b), or mir-20 (MSCV20), or a subcluster of mir-19a, mir-20 and mir-19b (MSCV19a-19b) in an MSCV retroviral vector (MSCV) or infected with a control MSCV virus (MSCVPIG) were monitored by blood smear analysis. The Kaplan-Meier curves represent percentage of leukemia-free survival or overall survival as indicated. Time is shown in days.

FIG. 9: shows Table 1 which provides immunophenotypes of tumors derived from c-myc cooperation with mir-18, mir-19b and mir19a-19b.

Figure 10:
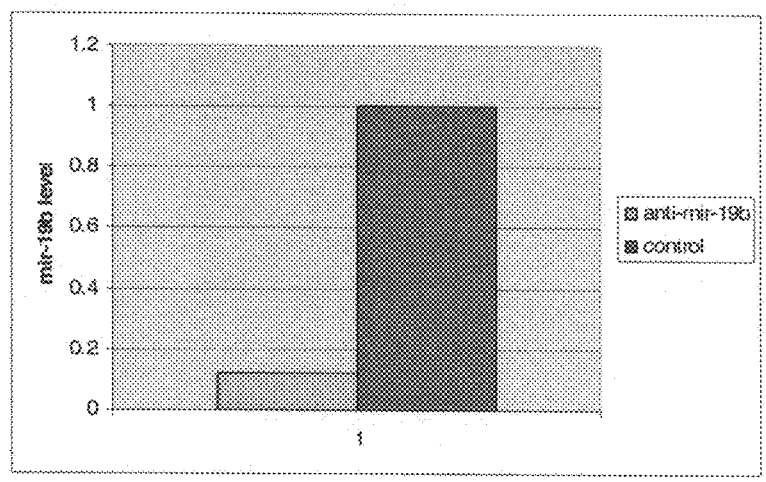

FIG. 10: Inhibition of the mir-19b miRNA level encoded by the mir17-92 cistron using an antisense oligonucleotide. The graph shows Mir-19b levels for Karpas1718 cells transfected with anti-mir19b or control oligos. The mir-19b level is measured by ABI taqman assay. The anti-mir-19b oligonucleotide was 2-O-methyl modified at every nucleotide residue and has the sequence ucaguuuugcauggauuugcaca (SEQ ID NO: 11). Similar experiments may be conducted using anti-mir-18 oligonucleotides having 2-O-methyl modifications at every residue and having the sequence uaucugcacuagaugcaccuua (SEQ ID NO: 12).

FIG. 11: Shows the DNA sequence of the human mir17-92 polycistron (SEQ ID NO: 1). The DNA sequences which encode for mir-17, mir-18, mir-19a, mir-20, mir-19b-1, and mir-92-1 microRNAs (from top to bottom in this order) are underlined and in capital letters. Mir-17 is encoded by nucleotide residues 84-167 of SEQ ID NO: 1, mir-18 is encoded by nucleotide residues 230-300 of SEQ ID NO: 1, mir-19a is encoded by nucleotide residues 370-451 of SEQ ID NO: 1, mir-20 is encoded by nucleotide residues 544-614, mir-19b-1 is encoded by nucleotide residues 671-757 of SEQ ID NO: 1, mir-92-1 is encoded by nucleotide residues 793-870 of SEQ ID NO: 1. The shaded regions show the portion of mir-18 (nucleotide residues 235-256 of SEQ ID NO: 1) targeted by the anti-mir-18 oligonucleotide discussed above and the portion of mir-19b (nucleotide residues 724-746 of SEQ ID NO: 1) targeted by the anti-mir-19b oligonucleotide discussed above.

DETAILED DESCRIPTION OF THE INVENTION

I. Overview

MicroRNA, or miRNA, is a class of small non-coding RNA molecules, that are capable of causing interference, inhibition of RNA translation into protein, and can cause post-transcriptional silencing of specific genes in cells and in the body (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002). To date, more than 200 microRNAs have been described in humans. However, the precise function of these regulatory, non-coding RNAs remains largely obscure.

The present invention is based, at least in part, on Applicants' novel discovery that the mir17-92 cistron, a microRNA cluster, is overexpressed in tumors and tumor cell lines. Importantly, Applicants have demonstrated that the full mir17-92 cistron as well as a truncated cluster comprising mir17-19b-1 ("mir17-19b") can act as an oncogene in vivo, as shown by their abilities to accelerate Eµ-myc or p53$^{-/-}$ induced tumorigenesis in mice (see more details in the Figures and Exemplification section). The mir17-92 cistron and the miRNAs encoded thereby can therefore be used for diagnosis, prognosis, rational drug design, and other therapeutic intervention of tumors and cancers. Accordingly, the present invention features therapeutic and preventative methods for cancers via decreasing the expression and/or activity of the one or more microRNAs encoded by the mir17-92 cistron. In certain preferred embodiments, the cancer therapeutic and preventative methods of the present invention decrease the expression and/or activity of the truncated cluster mir17-19b. In certain embodiments, the cancer therapeutic and preventative methods of the present invention decrease the expression and/or activity of miR-19b-1 and/or miR-18. As described in more detail below, Applicants have also devised screening methods to identify inhibitors of mir17-92 cistron expression as novel cancer therapeutic and preventative agents.

The term "a mir17-92 cistron inhibitor", as used herein, refers to an agent that decreases the expression and/or activity of one or more miRNAs encoded by the mir17-92 cistron, which include the following seven microRNAs: miR-17-5p, miR-17-3p, miR-18, miR-19a, miR-20, miR-19b-1 and miR-92-1. A mir17-92 cistron inhibitor includes an agent that decreases the level of expression of one or more miRNAs included in the mir17-92 cistron, by decreasing its expression at the transcriptional level, increasing its degradation, or a combination of both, either directly, or indirectly by modulating an upstream regulator of the mir17-92 cistron. A mir17-92 cistron inhibitor further includes an agent that interferes with the activity of one or more miRNAs encoded by the mir17-92 cistron, including, but not limited to, a non-functional miRNA that competes with at least one of the miRNAs encoded by the mir17-92 cistron for binding to the respective target gene(s). In certain embodiments, a mir17-92 cistron inhibitor specifically decreases the expression and/or activity of one or more miRNAs included in the truncated cluster mir17-19b, the vertebrate-specific portion of the mir17-92 cistron, such as miR-17-5p, miR-17-3p, miR-18, miR-19a, miR-20 and miR-19b-1. In certain embodiments, a mir17-92 inhibitor specifically decreases the expression and/or activity of one or more of miR19-b-1 and/or miR-18.

Suitable mir17-92 cistron inhibitors can be biological macromolecules such as nucleic acids or polypeptides, chemical compounds, mixtures of chemical compounds, or extracts isolated from bacterial, plant, fungal, or animal matter, each of which may be administered to a subject in need thereof via standard techniques known in the art. In certain embodiments, mir17-92 cistron inhibitors are antisense molecules that inhibit one or more miRNAs encoded by the mir17-92 cistron. Antisense molecules have been shown to be effective in inhibiting human miRNAs (see A. M. Cheng et al., Nucleic Acids. Research, 33: 1290-1297 (2005)). In certain other embodiments, mir17-92 cistron inhibitors are oligomeric compounds that can hybridize or sterically interfere with miRNAs encoded by the mir17-92 cistron. Methods of making such oligomeric compounds are described in the PCT application WO05013901, the entire content of which is incorporated herein.

The present invention also features diagnostic methods for cancers based on the expression of the mir17-92 cistron, and more preferably, the expression of the mir17-19b cistron. In certain embodiments, the invention features diagnostic methods for cancers based on the expression of one or more of miR19-b-1 and/or miR-18.

II. Definitions

As used herein, "cancer" refers to all types of cancers, or neoplasms or benign or malignant tumors. Preferred cancers for treatment using methods provided herein include B-cell malignancies, lymphomas, carcinoma, sarcoma, or leukemia. "Lymphoma" refers to a malignant growth of B or T cells in the lymphatic system. "Lymphoma" includes numerous types of malignant growths, including Hodgkin's Lymphoma and non-Hodgkin's lymphoma (NHL). "Non-Hodgkin's Lymphoma" refers to a malignant growth of B or T cells in the lymphatic system that is not a Hodgkin's Lymphoma (which is characterized, e.g., by the presence of Reed-Stemberg cells in the cancerous area). By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma.

A "B cell malignancy" refers to B cell lymphomas and leukemias, including, for example, Hodgkin's disease (all forms, e.g., relapsed Hodgkin's disease, resistant Hodgkin's disease), non-Hodgkin's lymphomas (low grade, intermediate grade, high grade, and other types), small lymphocytic/B cell chronic lymphocytic leukemia (SLL/B-CLL), ALL-L3 (Burkitt's type leukemia), chronic lymphocytic leukemia (CLL), chronic leukocytic leukemia, acute myelogenous leukemia, acute lymphoblastic leukemia, chronic lymphocytic leukemia, chronic myelogenous leukemia, lymphoblastic leukemia, lymphocytic leukemia, monocytic leukemia, myelogenous leukemia, promyelocytic leukemia, monocytic cell leukemias, lymhoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, and angioimmunoblastic lymphoadenopathy (see, Gaidono et al., "Lymphomas", In Cancer: Principles & Practice of Oncology, Vol. 2: 2131-2145 (DeVita et al., eds., 5$^{th}$ ed. 1997)).

The phrase "detecting a cancer" or "diagnosing a cancer" refers to determining the presence or absence of cancer or a precancerous condition in an animal. "Detecting a cancer" also can refer to obtaining indirect evidence regarding the likelihood of the presence of precancerous or cancerous cells in the animal or assessing the predisposition of a patient to the development of a cancer. Detecting a cancer can be accomplished using the methods of this invention alone, in combination with other methods, or in light of other information regarding the state of health of the animal.

The term "mammal" for purposes of treatment or diagnosis refers to any animal classified as a mammal, including humans, domestic and farm animals, and zoo, sports, or pet animals, such as dogs, horses, cats, cows, etc. In exemplary embodiments, a mammal is a human.

The term "precancerous" refers to cells or tissues having characteristics relating to changes that may lead to malignancy or cancer. Examples include adenomatous growths in colon, lung, ovarian, or breast, tissues, or conditions, for example, dysplastic nevus syndrome, a precursor to malignant melanoma of the skin. Examples also include, abnormal neoplastic, in addition to dysplastic nevus syndromes, polyposis syndromes, prostatic dysplasia, and other such neoplasms, whether the precancerous lesions are clinically identifiable or not.

A "tumor," as used herein, refers to all neoplastic cell growth and proliferation, whether malignant or benign, and all precancerous and cancerous cells and tissues.

III. Diagnostic Assays

The mir17-92 cistron and the miRNAs encoded thereby can be used for detection, diagnosis, prognosis, rational drug design, and other therapeutic intervention of tumors and cancers, including, for example, various kinds of lymphoma.

Detection and measurement of amplification and/or overexpression of the mir17-92 cistron, or one or more miRNAs encoded thereby, in a biological sample taken from a patient indicates that the patient may have developed a tumor. Particularly, the presence of amplification of the mir17-92 cistron is diagnostic for cancer or a precancerous condition, for example, a lymphoma, with high probability of accuracy. The present invention therefore provides, in one aspect, methods for diagnosing or characterizing a cancer or tumor in a mammalian tissue by measuring the level of expression of one or more of the miRNAs encoded by the mir17-92 cistron in samples taken from subject, and determining whether such miRNA is overexpressed in the sample. In another aspect, the invention provides methods for diagnosing or characterizing a cancer or tumor in a mammalian tissue by measuring the genomic copy number of the mir17-92 cistron, or a portion thereof, in samples taken from subject, and determining whether such genomic copy number is amplified in the sample. Various techniques for measuring and evaluating mRNA expression levels and genomic copy number are provided herein, including hybridization based and amplification based methods. Suitable samples for diagnosis of a subject may be blood, urine, serum, saliva, or tissue samples. In an exemplary, embodiment, a diagnostic sample may be a sample of the tissue under suspicion of being precancerous or cancerous, e.g., a biopsy sample, surgical sample, etc.

The presence of a target gene (e.g., the mir17-92 polycistron) that has undergone amplification in tumors may be evaluated by determining the copy number of the target genes, i.e., the number of DNA sequences in a cell encoding the target expression product. Generally, a normal diploid cell has two copies of a given autosomal gene. The copy number can be increased, however, by gene amplification or duplication, for example, in cancer cells, or reduced by deletion. Methods of evaluating the copy number of a particular gene or miRNA expression levels are well known in the art, and include, inter alia, hybridization and amplification based assays.

Any of a number of hybridization based assays can be used to detect the copy number of the mir17-92 cistron, or a portion thereof, in the cells of a biological sample. One such method is Southern blot (see Ausubel et al., or Sambrook et al., supra), where the genomic DNA is typically fragmented, separated electrophoretically, transferred to a membrane, and subsequently hybridized to a probe specific for the mir17-92 cistron. Comparison of the intensity of the hybridization signal from the probe for the target region with a signal from a control probe from a region of normal, nonamplified, single-copied genomic DNA in the same genome provides an estimate of the copy number of the mir17-92 cistron, or a portion thereof. An increased signal compared to the control represents the presence of amplification.

Another methodology for determining the copy number of the mir17-92 cistron, or a portion thereof, in a sample is in situ hybridization, for example, fluorescence in situ hybridization (FISH) (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

Another methodology for determining DNA copy number is comparative genomic hybridization (CGH). In comparative genomic hybridization methods, a "test" collection of nucleic acids is labeled with a first label, while a second collection (for example, from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the copy number of the mir17-92 cistron, or a portion thereof. A cytogenetic representation of DNA copy-number variation can be generated by CGH, which provides fluorescence ratios along the length of chromosomes from differentially labeled test and reference genomic DNAs.

Hybridization protocols suitable for use with the methods of the invention are described, for example, in Albertson (1984) EMBO J. 3:1227-1234; Pinkel (1988) Proc. Natl. Acad. Sci. USA, 85:9138-9142; EPO Pub. No. 430:402; Methods in Molecular Biology, Vol. 33: In Situ Hybridization Protocols, Choo, ed., Humana Press, Totowa, N.J. (1994).

Amplification-based assays also can be used to measure the copy number of the mir17-92 cistron, or a portion thereof. In such assays, the mir17-92 cistron nucleic acid sequence acts as a template in an amplification reaction (for example, Polymerase Chain Reaction or PCR). In a quantitative amplification, the amount of amplification product will be proportional to the amount of template in the original sample. Comparison to appropriate controls provides a measure of the copy number of the mir17-92 cistron, according to the principles discussed above. Methods of real-time quantitative PCR using TaqMan probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994.

A TaqMan-based assay also can be used to quantify the mir17-92 cistron polynucleotides, or portions thereof. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, world wide web 2 at perkin-elmer.com).

Other suitable amplification methods for determination of copy number include, but are not limited to, ligase chain reaction (LCR) (see, Wu and Wallace, Genomics, 4: 560, 1989; Landegren et al., Science, 241: 1077, 1988; and Barringer et al., Gene, 89:117, 1990), transcription amplification (Kwoh et al., Proc. Natl. Acad. Sci. USA, 86:1173, 1989), self-sustained sequence replication (Guatelli et al., Proc Nat Acad Sci, USA 87:1874, 1990), dot PCR, and linker adapter PCR, for example.

One powerful method for determining DNA copy number uses microarray-based platforms. Microarray technology may be used because it offers high resolution. For example, the traditional CGH generally has a 20 Mb limited mapping resolution; whereas in microarray-based CGH, the fluorescence ratios of the differentially labeled test and reference genomic DNAs provide a locus-by-locus measure of DNA copy-number variation, thereby achieving increased mapping resolution. Details of various microarray methods can be found in the literature. See, for example, U.S. Pat. No. 6,232,068; Pollack et al., Nat. Genet., 23(l):41-6, (1999), and others.

The hybridization and amplification based methods are described above with reference to DNA copy number of the mir17-92 polycistron. However, one of ordinary skill in the art will understand that such methods may also be used to determine the expression levels of one or more miRNAs encoded by the mir17-92 polycistron. For example, miRNA expression levels may be determined using, for example, Southern blotting, fluorescence in situ hybridization, comparative genomic hybridization, PCR (or RT-PCR), etc. Other methods are provided in the Exemplification section below.

The present invention also provides, in other aspects, methods for diagnosing a cancer or tumor in a mammalian tissue by measuring the DNA copy number of the mir17-92 cistron, or a portion thereof, in samples taken from the subject, and determining whether the mir17-92 cistron is amplified in the sample. In one embodiment, the sample may be a sample of the tissue of suspicion. The various techniques, including hybridization based and amplification based methods, for measuring and evaluating DNA copy numbers are provided herein as discussed above. The present invention thus provides methods for detecting amplified genes at the DNA level and increased expression at the RNA level, wherein both the results are indicative of tumor progression.

In certain embodiments, the diagnostic methods described herein involve comparison of a test sample to a control sample. For example, the methods may involve determining genomic copy number of the mir17-92 cistron, or a portion thereof, determining expression level of one or more miRNAs encoded by the mir17-92 cistron, or a portion thereof, and/or determining the activity level of one or more miRNAs encoded by the mir17-92 cistron, or a portion thereof, in a test sample (e.g., a sample from a subject who is to be diagnosed for cancer or a precancerous lesion). The genomic copy number, expression levels, and/or activity levels from the test subject may then be compared to the corresponding levels from a control sample. A control sample may be, for example, a sample taken from a subject not suffering from the same disease that the test subject is thought to be suffering from. Alternatively, a control sample may be a sample taken from the test individual at an earlier time point (e.g., before the test subject began exhibiting symptoms of the diseased state). Alternatively, a control sample may be a sample taken from another location within the test subject (e.g., if the subject is being tested for breast cancer, the control sample be taken from another location within the test subject other than the breast). Alternatively, the control sample may be a predetermined measurement determined for one or more persons, preferably a population of individuals, that is stored in a database, such as an electronic database.

IV. Drug Screening Assays

Also provided are numerous approaches to screen for mir17-92 cistron inhibitors and to evaluate mir17-92 cistron inhibitors for the ability to prevent and/or ameliorate tumors and cancer symptoms, including, for example, cell-based and animal model-based trial systems.

In one embodiment, the screening methods comprise first contacting a candidate agent with a cancer cell that expresses one or more miRNA members of the mir17-92 cistron, followed by determining the expression level of one or more members of the mir17-92 cistron in the cell to generate data for a test level. The test level of each miRNA member of the mir17-92 cistron is then compared to the respective level in the cancer cell prior to contacting the candidate agent. Alternatively, the test level of each miRNA member of the mir17-92 cistron may be compared to the respective level in a cancer cell that has been treated with an agent having a known activity or no activity (e.g., a control agent). A decrease in the level of one or more miRNA members of the mir17-92 cistron in the test level indicates that the candidate agent is an inhibitor of the mir17-92 cistron and a potential cancer therapeutic agent.

A variety of assay formats will suffice and, in light of the present disclosure, those not expressly described herein will nevertheless be comprehended by one of ordinary skill in the art. Agents to be tested for their ability to act as mir17-92 cistron inhibitors can be produced, for example, by bacteria, yeast, plants or other organisms (e.g., natural products), produced chemically (e.g., small molecules, including peptidomimetics), or produced recombinantly. Test agents contemplated by the present invention include non-peptidyl organic molecules, peptides, polypeptides, peptidomimetics, sugars, hormones, and nucleic acid molecules (such as antisense, ribozymes or RNAi nucleic acid molecules). In a preferred embodiment, the test agent is a small organic molecule having a molecular weight of less than about 2,000 daltons.

The test agents can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps.

In some cases, one or more compounds can be tested simultaneously. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., Proc. Natl. Acad. Sci. USA 90:10922-10926 (1993) and DeWitt, S. H. et al., Proc. Natl. Acad. Sci. USA 90:6909-6913 (1993), relating to tagged compounds; see also, Rutter, W. J. et al., U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure is an exemplary method that can be used to identify individual compounds selected by the methods described herein.

In addition, animal models can be used to identify compounds for use as drugs and pharmaceuticals that are capable of treating or suppressing symptoms of tumors and cancers. For example, animal models can be exposed to a test compound at a sufficient concentration and for a time sufficient to elicit such an amelioration in the exposed animals. The response of the animals to the exposure can be monitored by assessing the reversal of symptoms associated with the tumor or cancer, by evaluating changes in DNA copy number of the mir17-92 cistron, or a portion thereof, in cell populations, and/or by evaluating levels of expression of one or more miRNAs encoded by the mir17-92 cistron. Any treatments which reverse one or more symptoms of tumors and cancers, which reduce overexpression of one or more miRNAs encoded by the mir17-92 cistron, and/or which reduce DNA copy number of the mir17-92 cistron, or a portion thereof, may be considered as candidates for therapy in humans. Dosages of test agents can be determined by deriving dose-response curves.

Moreover, fingerprint patterns or gene expression profiles can be characterized for known cell states, for example, normal or known pre-neoplastic, neoplastic, or metastatic states, within the cell- and/or animal-based model systems. Subsequently, these known fingerprint patterns can be compared to ascertain the ability of a test compound to modify such fingerprint patterns, and to cause the pattern to more closely resemble that of a normal fingerprint pattern. For example, administration of a compound which affects the expression of one or more miRNAs encoded by the mir17-92 cistron may cause the fingerprint pattern of a precancerous or cancerous model system to more closely resemble a control (or normal) system; such a compound thus will have therapeutic utilities in treating the cancer. In other situations, administration of a compound may cause the fingerprint pattern of a control system to begin to mimic tumors and cancers (for example, breast cancer, colon cancer, lung cancer, or ovarian cancer); such a compound therefore acts as a tumorigenic agent, which in turn can serve as a target for therapeutic interventions of the cancer and its diagnosis.

In certain embodiments, the drug screening assays described herein comprise determining the expression level and/or activity level of one or more miRNAs encoded by the mir17-92 cistron, or a portion thereof, in a cell contacted with a candidate agent and comparing those levels to a control level. In various embodiments, the control level may be the expression level and/or activity level of one or more miRNAs encoded by the mir17-92 cistron, or a portion thereof, in a cell not contacted with the test agent, in the same cell before being contacted with the test agent, or in a cell contacted with a test agent having a known activity.

V. Agents and Methods for Treating Cancers

The mir17-92 cistron inhibitors identified in the present invention, such as by the assays described above, can be used to generate compositions, e.g., suitable for use in human patients, for treating or preventing cancer.

In certain embodiments, the mir17-92 cistron inhibitor of the present invention is a small organic molecule, e.g., has a molecular weight less than 2000 amu, and even more preferably less than 1500 amu or even 1000 amu. Preferably the agent is cell-permeable. In certain preferred embodiments, the agent is also orally active. Candidate small molecule compounds can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant, and animal extracts are available or readily produced. Additionally, natural or synthetically produced libraries and compounds can be modified through conventional chemical, physical, and biochemical means. Known pharmacological agents may be subjected to directed or random chemical modifications, such as acylation, alkylation, esterification, and amidification, to produce structural analogs.

In certain aspects, the mir17-92 cistron inhibitors of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the mir17-92 cistron or an miRNA encoded thereby.

In certain other embodiments, the mir17-92 cistron inhibitors of the present invention include antisense nucleic acids. In one embodiment, the invention relates to the use of antisense nucleic acids which inhibit expression of one or more members of the mir17-92 cistron. Such antisense nucleic acids can be delivered, for example, as an expression plasmid which, when transcribed in the cell, produces an oligonucleotide which is complementary to at least a unique portion of the one or more mature miRNAs encoded by the mir17-92 cistron. Alternatively, the construct is an oligonucleotide which is generated ex vivo and which, when introduced into the cell causes inhibition of expression by hybridizing with the miRNAs and/or genomic sequences encoding such miRNAs. Such oligonucleotide probes are optionally modified oligonucleotides which are resistant to endogenous nucleases, e.g., exonucleases and/or endonucleases, and are therefore stable in vivo. Antisense molecules have been shown to be effective in inhibiting human miRNAs (see A. M. Cheng et al., Nucleic Acids. Research, 33: 1290-1297 (2005)).

In certain embodiments, the antisense oligonucleotides of the invention are complementary to the guide strand of the miRNA positioned in the RNA silencing complex. In certain embodiments, the antisense oligonucleotides comprise one or more 2'-O-methyl nucleotides. In certain embodiments, the antisense oligonucleotides comprise at least one 2'-O-methyl oligonucleotide at one or both ends (e.g., 3' and/or 5' ends). In certain embodiments, the antisense oligonucleotides are fully modified 2'-O-methyl oliogonucleotides. In certain embodiments, the antisense oligonucleotides comprise one or more 2'-O-methyl ribonucleotides. In certain embodiments, the antisense oligonucleotides are fully modified 2'-O-methyl oligoribonucleotides. In certain embodiments, the invention provides an antisense oligonucleotide targeted to miR19-b-1 and/or miR-18.

Antisense nucleic acids include non-enzymatic nucleic acid compounds that bind to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In addition, antisense DNA can be used to target nucleic acid by means of DNA-RNA interactions, thereby activating RNase H, which digests the target nucleic acid in the duplex. The antisense oligonucleotides can comprise one or more RNAse H activating region, which is capable of activating RNAse H to cleave a target nucleic acid. Antisense DNA can be synthesized chemically or expressed via the use of a single stranded DNA expression vector or equivalent thereof. An RNase H activating region refers to a region (generally greater than or equal to 4-25 nucleotides in length, preferably from 5-11 nucleotides in length) of a nucleic acid compound capable of binding to a target nucleic acid to form a non-covalent complex that is recognized by cellular RNase H enzyme (see for example Arrow et al., U.S. Pat. No. 5,849,902; Arrow et al., U.S. Pat. No. 5,989,912). The RNase H enzyme binds to a nucleic acid compound-target nucleic acid complex and cleaves the target nucleic acid sequence.

The RNase H activating region comprises, for example, phosphodiester, phosphorothioate, phosphorodithioate, 5'-thiophosphate, phosphoramidate or methylphosphonate backbone chemistry, or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the RNase H activating region and the instant disclosure.

Thus, the antisense nucleic acids of the disclosure include natural-type oligonucleotides and modified oligonucleotides including phosphorothioate-type oligodeoxyribonucleotides, phosphorodithioate-type oligodeoxyribonucleotides, methylphosphonate-type oligodeoxyribonucleotides, phosphoramidate-type oligodeoxyribonucleotides, H-phosphonate-type oligodeoxyribonucleotides, triester-type oligodeoxyribonucleotides, alpha-anomer-type oligodeoxyribonucleotides, peptide nucleic acids, other artificial nucleic acids, and nucleic acid-modified compounds.

Other modifications include those which are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3',5'-substituted oligonucleotide having a sugar which, at both its 3' and 5' positions is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O-lower alkyl group containing 1-6 saturated or unsaturated carbon atoms, or with an —O-aryl, or allyl group having 2-6 carbon atoms wherein such —O-alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. Nonlimiting examples of particularly useful oligonucleotides of the disclosure have 2'-O-alkylated ribonucleotides at their 3', 5', or 3' and 5' termini, with at least four or five contiguous nucleotides being so modified. Examples of 2'-O-alkylated groups include, but are not limited to, 2'-O-methyl, 2'-O-ethyl, 2'-O-propyl, and 2'-O-butyls.

In certain cases, the synthesis of the natural-type and modified antisense nucleic acids can be carried out with, for example, a 381A DNA synthesizer or 394 DNA/RNA synthesizer manufactured by ABI (Applied Biosystems Inc.) in accordance with the phosphoramidite method (see instructions available from ABI, or F. Eckstein, Oligonucleotides and Analogues: A Practical Approach, IRL Press (1991)). In the phosphoramidite method, a nucleic acid-related molecule is synthesized by condensation between the 3'-terminus of a modified deoxyribonucleoside or modified ribonucleoside and the 5'-terminus of another modified deoxyribonucleoside, modified ribonucleoside, oligo-modified deoxyribonucleotide or oligo-modified-ribonucleotide by use of a reagent containing phosphoramidite protected with a group such as cyanoethyl group. The final cycle of this synthesis is finished to give a product with a protective group (e.g., dimethoxytrityl group) bound to a hydroxyl group at the 5'-terminus of the sugar moiety. The oligomer thus synthesized at room temperature is cleaved off from the support, and its nucleotide and phosphate moieties are deprotected. In this manner, the natural-type oligonucleic acid compound is obtained in a crude form. The phosphorothioate-type nucleic acids can also be synthesized in a similar manner to the above natural type by the phosphoramidite method with the synthesizer from ABI. The procedure after the final cycle of the synthesis is also the same as with the natural type.

The crude nucleic acids (natural type or modified) thus obtained can be purified in a usual manner e.g., ethanol precipitation, or reverse phase chromatography, ion-exchange chromatography and gel filtration chromatography in high performance liquid chromatography (HPLC), supercritical fluid chromatography, and it may be further purified by electrophoresis. A cartridge for reverse phase chromatography, such as tC 18-packed SepPak Plus (long body/ENV) (Waters), can also be used. The purity of the natural-type and modified (e.g., phosphorothioate-type) nucleic acids can be analyzed by HPLC.

In another embodiment, the invention relates to the use of RNA interference (RNAi) to reduce expression of one or more miRNAs encoded by the mir17-92 cistron. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. RNAi provides a useful method of inhibiting gene expression in vitro or in vivo. RNAi constructs can comprise either long stretches of dsRNA identical or substantially identical to the target nucleic acid sequence or short stretches of dsRNA identical to or substantially identical to only a region of the target nucleic acid sequence.

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo. In certain embodiments, the RNAi constructs are non-enzymatic nucleic acids.

Optionally, the RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA so that it has the ability to mediate RNAi. Thus, the RNAi constructs described herein have the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, 96%, 97%, 98%, or 99% sequence identity, or even 100% sequence identity, between the inhibitory RNA and the portion of the target gene is preferred. Alternatively, the duplex region of the RNA may be defined functionally as a nucleotide sequence that is capable of hybridizing under specified conditions with a portion of the target gene transcript (e.g., 400 mM NaCl, 40 mM PIPES pH 6.4, 1 mM EDTA, 50° C. or 70° C. hybridization for 12-16 hours; followed by washing).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

The subject RNAi constructs can be "small interfering RNAs" or "siRNAs." These nucleic acids are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from a Drosophila embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with an antibody can be used to purify siRNAs.

Alternatively, the RNAi construct is in the form of a hairpin structure (referred to as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In another embodiment, the invention relates to the use of ribozyme molecules designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591. The ribozymes of the present invention also include RNA endoribonucleases (hereinafter "Cech-type ribozymes") such as the one which occurs naturally in Tetrahymena thermophila (known as the IVS or L-19 IVS RNA) and which has been extensively described (see, e.g., Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216).

In a further embodiment, the invention relates to the use of DNA enzymes to inhibit expression of one or more miRNAs encoded by the mir17-92 cistron. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. Briefly, to design an ideal DNA enzyme that specifically recognizes and cleaves a target nucleic acid, one of skill in the art must first identify the unique target sequence. Preferably, the unique or substantially unique sequence is a G/C rich region of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

Depending on the nature of the disease (condition) and the therapy, administration of the cancer therapeutic agents of the invention may be continued while the other therapy is being administered and/or thereafter. Administration of the cancer therapeutic agents may be made in a single dose, or in multiple doses. In some instances, administration of the cancer therapeutic agent is commenced at least several days prior to the conventional therapy, while in other instances, administration is begun either immediately before or at the time of the administration of the conventional therapy.

In a further embodiment, the invention relates to the use of nucleic acid aptamers to inhibit expression of one or more miRNAs encoded by the mir17-92 cistron. A nucleic acid aptamer is a nucleic acid or a nucleic acid-like molecule that is capable of binding to a specific molecule of interest with high affinity and specificity. A nucleic acid aptamer also can be a nucleic acid molecule that mimics the three dimensional structure of active portions of one or more of the miRNAs encoded by the mir17-92 cistron. A nucleic acid-aptamer is typically between about 9 and about 300 nucleotides or the like in length. More commonly, an aptamer is between about 30 and about 100 nucleotides or the like in length. Nucleic acid-aptamers may be prepared by any known method, including synthetic, recombinant, and purification methods (James W., Current Opinion in Pharmacology, 1:540-546 (2001); Colas et al., Nature 380:548-550 (1996)).

According to one aspect of the invention, aptamers of the instant invention include non-modified or chemically modified RNA, DNA, PNA or polynucleotides. The method of selection may be by, but is not limited to, affinity chromatography and the method of amplification by reverse transcription (RT) or polymerase chain reaction (PCR). Aptamers have specific binding regions which are capable of forming complexes with an intended target molecule in an environment wherein other substances in the same environment are not complexed to the nucleic acid.

The invention also provides nucleic acids (for example, mRNA molecules) that include an aptamer as well as a coding region for a regulatory polypeptide. The aptamer is positioned in the nucleic acid molecule such that binding of a ligand to the aptamer prevents translation of the regulatory polypeptide.

In another aspect, the present invention provides methods for treating or controlling a cancer or tumor and the symptoms associated therewith. Any of the agents, for example, those identified in the aforementioned assay systems, can be tested for the ability to prevent and/or ameliorate symptoms of tumors and cancers. As used herein, inhibit, control, ameliorate, prevent, treat, and suppress collectively and interchangeably mean stopping or slowing cancer formation, development, or growth and eliminating or reducing cancer symptoms.

In certain embodiments, a mir17-92 cistron inhibitor may be administered as part of a combination therapy. In certain embodiments, a combination therapy may comprise administration of two or more mir17-92 cistron inhibitors as described herein. In certain embodiments, a combination therapy comprises two or more nucleic acid inhibitors (e.g., antisense, ribozyme, or RNAi constructs, or combinations thereof). In an exemplary embodiment, a combination therapy comprises antisense nucleic acids targeted to miR19-b-1 and miR-18. In certain embodiments, the invention provides a combination therapy comprising a mir17-92 cistron inhibitor and a convention chemotherapeutic agent, such as, for example, paclitaxel, arabinoside, 5-FU, cisplatin, etc. Other chemotherapeutic agents are described, for example, in U.S. Patent Application Publication No. 2005/0112060. In another embodiment, the invention provides a combination therapy for treatment of a B-cell malignancy comprising one or more mir17-92 inhibitors and an anti-CD20 monoclonal antibody or an anti-CD22 monoclonal antibody. Examples of CD20 monocolonal antibodies include, for example, Rituximab™. Examples of CD22 monoclonal antibodies are described, for example, in U.S. Pat. No. 5,789,557 and PCT Publication Nos. WO 98/42378, WO 00/20864, and WO 98/41641.

VI. Methods for Monitoring Efficacy of Cancer Treatment

In one aspect, the present invention provides methods for monitoring the efficacy of a therapeutic treatment regimen of cancer and methods for monitoring the efficacy of a compound in clinical trials or other research studies for inhibition of tumors. The monitoring can be accomplished by detecting and measuring, in the biological samples taken from a patient at various time points during the course of the application of a treatment regimen for treating a cancer or a clinical trial or other research studies, the changed levels of expression of one or more miRNAs encoded by the mir17-92 cistron or amplification of the mir17-92 cistron, in the cell population or sample. A level of expression and/or amplification that is lower in samples taken at the later time of the treatment or trial or a research study than those at the earlier date indicates that the treatment regimen is effective to control the cancer in the patient, or the compound is effective in inhibiting the tumor. In contrast, samples taken at the later time of the treatment or trial or a research study showing no statistically significant decrease in level of expression and/or amplification than those at the earlier date indicates that the treatment regimen is not effective to control the cancer in the patient, or the compound is not effective in inhibiting the tumor. Of course, the time course studies should be so designed that sufficient time is allowed for the treatment regimen or the compound to exert any effect it may have.

Therefore, the influence of compounds on tumors and cancers can be monitored both in a clinical trial or other research studies and in a basic drug screening. In a clinical trial or other research studies, for example, a sample may be obtained from a subject and RNA prepared and analyzed by Northern blot analysis or TaqMan RT-PCR as described herein. Suitable samples include, for example, blood, urine, saliva, serum, or tissue samples. In certain embodiments, tumor cells can be isolated from the tissue in question, such as breast, colon, lung, or ovarian tumor by biopsy or surgery. The fingerprint expression profiles or the miRNAs thus generated can serve as putative biomarkers for a variety of cancers including, breast, colon, lung, or ovarian cancer or B-cell or T-cell malignancies. Particularly, the expression of one or more miRNAs encoded by the mir17-92 cistron serves as one such biomarker. Thus, by monitoring the level of expression of one or more miRNAs that are differentially-expressed or overexpressed from the mir17-92 cistron, an effective treatment protocol can be developed using suitable chemotherapeutic anticancer drugs or one or more of the mir17-92 cistron inhibitors described herein.

VII. Pharmaceutical Formulations

The compositions of this invention can be formulated and administered to inhibit a variety of disease states by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the present invention may be formulated in conventional manner using one or more physiologically acceptable carriers or excipients. The therapeutic compositions of the invention can be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the therapeutic compositions of the invention can be formulated in liquid solutions, preferably in physiologically compatible buffers such as Hank's solution or Ringer's solution. In addition, the therapeutic compositions may be formulated in solid form and redissolved or suspended immediately prior to use. Lyophilized forms are also included.

For oral administration, the therapeutic compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active agent. For buccal administration the therapeutic compositions may take the form of tablets or lozenges formulated in a conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflate or may be formulated containing a powder mix of the therapeutic agents and a suitable powder base such as lactose or starch.

The therapeutic compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the therapeutic compositions may also be formulated as a depot preparation. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

The therapeutic compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

A composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

The dosage administered will be a therapeutically effective amount of the compound sufficient to result in amelioration of symptoms of the bone disease and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Toxicity and therapeutic efficacy of therapeutic compositions of the present invention can be determined by standard pharmaceutical procedures in cell cultures or experimental animals, e.g., for determining The LD50 (The Dose Lethal To 50% Of The Population) And The ED50 (the dose therapeutically effective in 50% of the population). The dose ratio between toxic and therapeutic effects is the therapeutic index and it can be expressed as the ratio LD50/ED50. Therapeutic agents which exhibit large therapeutic induces are preferred. While therapeutic compositions that exhibit toxic side effects may be used, care should be taken to design a delivery system that targets such therapeutic agents to the site of affected tissue in order to minimize potential damage to uninfected cells and, thereby, reduce side effects.

The data obtained from cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized. For any agents used in the method of the invention, the therapeutically effective dose can be estimated initially from cell culture assays. A dose may be formulated in animal models to achieve a circulating plasma concentration range that includes the IC50 (i.e., the concentration of the test therapeutic agent which achieves a half-maximal inhibition of symptoms or inhibition of biochemical activity) as determined in cell culture. Such information can be used to more accurately determine useful doses in humans. Levels in plasma may be measured, for example, by high performance liquid chromatography.

It is understood that appropriate doses of small molecule agents depends upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.

These methods described herein are by no means all-inclusive, and further methods to suit the specific application will be apparent to the ordinary skilled artisan. Moreover, the effective amount of the compositions can be further approximated through analogy to compounds known to exert the desired effect.

The practice of aspects of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986). All patents, patent applications and references cited herein are incorporated in their entirety by reference.

EXEMPLIFICATION

The invention now being generally described, it will be more readily understood by reference to the following examples, which are included merely for purposes of illustration of certain aspects and embodiments of the present invention, and are not intended to limit the invention.

MicroRNAs (miRNAs) have emerged relatively recently as a novel class of small, non-coding RNAs (ncRNAs) that regulate gene expression. Nascent primary miRNA transcripts (pri-miRNAs) are processed sequentially by two ribonuclease III enzymes, Drosha and Dicer[2,3] to yield mature miRNAs, ranging from 18 nt to 24 nt in length. MiRNAs are incorporated into the RNAi effector complex, RISC, and target specific mRNAs for translational repression or mRNA cleavage[4-6]. While hundreds of miRNAs have been cloned and/or predicted, only a handful have been functionally characterized. For example, lin-4 and let-7 regulate the timing of larval development in *C. elegans*[7,8]. lsy-6 and mir-273 control left/right asymmetric gene expression in *C. elegans* chemosensory neurons[9,10]. Bantam stimulates cell growth and prevents apoptosis in *Drosophila*[11], and miR181 potentiates B-cell differentiation in mammals[12]. These findings, in combination with computational target predictions, are consistent with miRNAs regulating a broad spectrum of physiologic and developmental processes.

Microarray-based expression studies have indicated specific alterations in miRNA expression profiles that correlate with particular tumor phenotypes (J. M. T. and S. M. H., unpublished). Among those that show altered expression, the mir1792 cistron is located at 13q31, a genomic locus that is amplified in cases of diffuse large B-cell lymphoma, follicular lymphoma, mantle cell lymphoma, primary cutaneous B-cell lymphoma and several other tumor types[1,13]. There are only 2 annotated genes in the epicenter of this amplicon, c13orf25 and GPC5. Previous studies showed that c13orf25 is the only one of these whose increased expression universally correlates with the presence of the amplicon[1]. Therefore, c13orf25 had been implicated as a target of the 13q31 amplicon[1]. It is unlikely that c13orf25 actually encodes a protein, since predicted ORFs encode only short peptides (<70 a.a.), which are not conserved in closely related species. Instead, the c13orf25 transcript appears to be the functional precursor of a series of seven microRNAs, miR-17-5p, miR-17-3p, miR-18, miR-19a, miR-20, miR-19b-1 and miR-92-1 (FIG. 1A). Additionally this cluster is related to the homologous mir106a-92 cluster on chromosome X and the mir106b-25 cluster on chromosome 7[14] (FIG. 1A). Alignment of the human c13orf25 locus and its murine ortholog revealed extensive sequence conservation only within the mir17-92 polycistron and its immediate flanking sequence. Several of the ESTs derived from c13orf25 and its mouse ortholog terminate at the 3' end of mir17-92 cluster, consistent with the presence of a Drosha processing site at this location (FIG. 1B).

A principal consequence of 13q31-q32 amplification could be an elevation of the mature miRNA species from the mir17-92 cluster. We acquired four cell lines previously described as carrying amplifications in the 13q31-q32 region[1] and confirmed the gene dosage increase at the c13orf25 locus in three of those cell lines using QPCR analysis. The abundance of 191 mature miRNA was assessed in these four cell lines and compared to normal B-cells and to five leukemia and lymphoma cell lines lacking the amplicon (FIG. 1C; FIG. 4). Using SAM analysis (Significance Analysis of Microarrays)[15], we identified six miRNAs whose high-level expression correlated with increased gene dosage of c13orf25 (Table 2). Five were from the mir17-92 cistron, and the sixth, miR-106a, is probably identified as a result of cross hybridization to miR-17-5p, from which it differs at only two terminal nucleotides (FIG. 1C). This hypothesis is supported by the observation that the mir106a-92 locus does not show copy number alterations in these cell lines (not shown). In each cell line, expression levels correlated with the copy number of the mir17-92 locus (FIG. 1C, lower panel). We also examined the expression of the mir17-92 precursor in a series of human tumor samples comprising both lymphomas and colorectal carcinomas. Of 46 lymphoma samples, including 13 diffuse large B-cell lymphomas and 6 follicular lymphomas, we saw significant (>5 fold) overexpression in 65% of the samples. Considering all of the B-cell lymphoma samples analyzed, the average increase in pri-miRNA expression was ~10-fold (FIG. 1D). In contrast, colorectal carcinomas rarely showed overexpression of the pri-miRNA. In this case, increases in expression from this locus were less common (15% samples exhibiting>5 fold upregulation) and the degree of overexpression was substantially lower (FIG. 1D).

Considered together, our data prompted the hypothesis that mir17-92 might contribute to tumor development. To test this idea directly, we used a mouse model of human B-cell lymphoma. Transgenic animals carrying a c-myc oncogene, driven by the immunoglobulin heavy chain enhancer (Eμ), develop B-cell lymphomas by 4-6 months of age[16]. Similarly, hematopoietic stem cells (HSCs) derived from fetal livers of Eμ-myc transgenics generate B-cell lymphomas with comparable latency when transplanted into lethally irradiated recipients (FIG. 2A)[17-20].

We therefore infected Eμ-myc/+ HSCs with a MSCV retrovirus that directs expression of a truncated cluster comprising mir17-19b-1 (hereafter mir1719b), the vertebrate-specific portion of the mir17-92 miRNA cistron (FIG. 1A). This virus also contained a GFP transgene, allowing us to follow infected stem cells in vitro and in vivo (FIG. 2A). Mice reconstituted with Eμ-myc/+ HSCs carrying a control MSCV vector developed lymphomas after the expected latency (3-6 months) with incomplete penetrance (FIG. 2B). Similarly, we examined >40 animals reconstituted with Eμ-myc/+ HSCs expressing subsets of 96 different single microRNAs (Table 3). Although we did not confirm miRNA overexpression in each case, we did not observe any significantly accelerated onset of disease. In contrast, 100% of the animals co-expressing the mir17-19b polycistron and c-myc developed leukemias at an average of 51 days following transplantation (standard deviation=13 days, p<0.0001 compared to MSCV controls using the Logrank test) and eventually died of B-cell lymphomas at an average age of 65 days (standard deviation=13 days, p<0.0001 compared to MSCV controls; FIG. 2B). In all but one case, primary lymphomas could be visualized by virtue of the linked GFP marker (FIG. 2C, Table 1). The mature miRNAs from the mir17-19b cluster exhibit high level expression in these tumors, as compared with miRNAs from the paralogous mir106a-92 locus and similar expression levels of mir17-19b as compared to the Karpas 1718 lymphoma cell line, which has increased c13orf25 gene dosage (FIG. 5). The full mir17-92 cistron was also tested in a small cohort of animals. While these gave similar results to those reconstituted with HSCs expressing mir17-19b, studies in cell lines indicated that the construct used to express the entire cluster gave lower levels of mature miRNAs, causing us to focus the majority of our study on the truncated mir17-19b cluster. Although studies are ongoing, we have yet to find any individual member of the mir17-19b cluster that can accelerate tumor formation to the extent seen with the intact polycistron (not shown).

The Eµ-Myc/mir17-19b lymphomas are true malignancies rather than hyperplasias, since primary tumor cells, when transplanted into C57B6/J recipients, induce B-cell lymphomas in 2-3 weeks that result in lethality after 4-5 weeks (data not shown). The secondary tumors exhibit pathological features indistinguishable from the original tumors, and retain tumorigenic potential after two additional rounds of serial transplantation (data not shown). Therefore, a microRNA cluster can accelerate Eµ-myc induced tumorigenesis in mice.

The pathological hallmarks of Eµ-myc/mir17-19b mosaic animals included massive enlargement of lymph nodes, splenic hyperplasia, infiltration of the thymus by lymphoma cells, and leukemia (FIG. 2C). Animals with advanced lymphomas displayed extramedullary hematopoiesis due to functional failure of the bone marrow. Furthermore, 6 out of 14 animals exhibited hind limb paralysis, associated with substantial tumor growth at the lumbar node. Tumors resulting from combined c-myc and mir17-19b expression consistently invade visceral organs outside the lymphoid compartment, including liver, lung, and occasionally, kidney (FIG. 2C, Table 1 and FIG. 3B). Additionally, Eµ-myc/mir17-19b lymphomas show a high mitotic index without extensive apoptosis (FIG. 3A). This contrasts with the Eµ-myc/MSCV tumors lacking the microRNA cluster, which show a high degree of apoptosis (FIG. 3A). These findings indicate that cooperation between Eµ-myc and mir17-19b gives rise to highly malignant, disseminated lymphomas capable of evading normal apoptotic responses to inappropriate proliferation.

Eµ-myc-induced lymphomas originate from the B-lymphoid lineage, yet the developmental characteristics of these tumor cells are not stage specific, as they can resemble either mature B-cells or pre-B cells. To examine the cell lineage of the Eµ-myc/mir17-19b lymphomas, we assessed the expression of cell surface markers, including a B-cell specific marker, B220, and T-cell specific markers, CD4 and CD8a. Not surprisingly, all tumors were of B-cell origin, staining positive for B220 and negative for both CD4 and CD8a (FIG. 3C and Table 1). We next analyzed these tumors for CD19 and IgM expression to distinguish pre-B from mature B cells. With one exception, Eµ-myc/mir17-19b lymphomas were derived purely from the pre-B cell lineage (Thy1$^{low}$CD19$^+$B220$^+$IgM$^-$) (Table 1), suggesting that overexpression of mir17-19b strongly favors transformation of B-cell progenitors under our experimental conditions.

Without wishing to be bound by theory, studies of tumor pathology suggest that increased expression of this cluster mitigates the pro-apoptotic response to elevated myc expression in vivo. Additionally, we have previously shown this miRNA cistron is highly expressed in embryonic stem cells, with its expression decreasing during embryonic development in mice[21]. It is, therefore, possible that these miRNAs promote 'stem' properties or specify characteristics of early developmental lineages.

Previous circumstantial evidence has indicated the potential involvement of a number of miRNAs in tumorigenesis. Although miRNAs only represent 1% of the mammalian genome, more than 50% of miRNA genes are located within regions associated with amplification, deletion and translocation in cancer[22]. Expression studies of various tumor types have also revealed specific alterations in miRNA profiles[22-25]. For example, mir-15 and mir-16 are frequently deleted and/or down-regulated in B-cell chronic lymphocytic leukemia[26]; miR-143 and miR-145 exhibit decreased expression in colorectal neoplasia[25], and miR-155 and its ncRNA host gene, BIC, are up-regulated by 100 fold in Burkitt's lymphoma patients Here we have shown that one miRNA polycistron is not only the subject of tumor-specific amplification, but that it is also overexpressed in tumors and tumor cell lines and can act as an oncogene in vivo. Our results indicate that non-coding RNAs may act as integral parts of the molecular architecture of oncogene and tumor suppressor networks.

Methods miRNA Expression Profiling

5 µg total RNA was labeled with RNA ligase and a Cy3-conjugated dinucleotide, and hybridized to custom oligonucleotide microarrays, as described in Thomson et al[21]. Cy3 median intensity values were filtered to remove data points in which did not exceed 2× background. Values were log-transformed (base 2) and median centered by array. Clustering was performed using the Cluster program from Stanford University using values that were median centered by gene. Dendrograms and expression maps were generated by the Treeview program from Stanford.

Cell Lines

The measurement of miRNA abundance was carried out using Karpas 1718 (derived from splenic lymphoma with villous lymphocytes, kindly provided by A. Karpas, University of Cambridge, UK), OCI-Ly4, OCI-Ly7, and OCI-Ly8 (derived from diffuse large B-cell lymphoma, kindly provided by R. Della-Favera, Columbia University). The cell lines lacking the 13q31-q32 amplicon were Raji (B-cell, derived from Burkitt's lymphoma, ATCC), Namalwa (B-cell, derived from Burkitt's lymphoma, ATCC), HG 1125 (EBV transformed human lymphoblastoid, kindly provided by B. Stillman, Cold Spring Harbor Laboratory), Manca (lymphoblast-like, derived from chronic myelogenous leukemia), Jurkat, proliferating B-cells (spleenic B-cells isolated from C57B6/Ly5.2 mouse and stimulated to proliferate in culture with Lipopolysaccharide), and normal B cells (derived from cord blood, Cambrex, N.J.).

RT-QPCR Analysis and Copy Number Analysis

Tumor samples were obtained from the Cooperative Human Tissue Network, USA (world wide web at chtn.ims.nci.nih.gov). Corresponding normal tissue RNA from 5 individuals was purchased from Biochain Institute Inc (Hayward, Calif.). For the fluorogenic real-time PCR, primers that amplify the mir17-92 pri-miRNA and the control β-actin mRNA probes were designed with Primer Express software (V.2): mir17-92 forward primer, CAGTAAAGGTAAG-GAGAGCTCAATCTG (SEQ ID NO: 2), mir17-92 reverse primer, CATACAACCACTAAGCTAAAGAATAATCTGA (SEQ ID NO: 3) and mir17-92 probe, (6-FAM)-TG-GAAATAAGATCATCATGCCCACTTGAGAC-(TAMRA) (SEQ ID NO: 4), β-actin forward primer, GCAAAGACCT-GTACGCCAACA (SEQ ID NO: 5); β-actin reverse primer, TGCATCCTGTCGGCAATG (SEQ ID NO: 6); β-actin probe, (6-FAM)-TGGCGGCACCACCATGTACC-(TAMRA) (SEQ ID NO: 7). The ratios of RNA species detected by mir17-92 primers and β-actin primers in each RNA sample were determined in triplicate by RT-QPCR using an ABI 7900HT Taqman sequence detector following the Standard Curve method. Subsequently, all values were normalized with the averaged ratio of the 5 corresponding normal samples. For DNA copy number determination using ABI 7900HT sequence detector, we performed QPCR analysis using the same mir17-92 primer set described above, and normalized the data against a reference probe corresponding to chromosomal region 6p22 (forward primer, GGTCTC-TATTTGCACTTGGCTGAT (SEQ ID NO: 8); reverse primer, TTTTCATTGTTGACCAAGCTAGACA (SEQ ID NO: 9); probe, (6-FAM)-TAGGGCATACTGCCTG-CATATTTCCTGCT-(TAMRA) (SEQ ID NO: 10)) or a β-actin probe. The reported values represent the ratios of DNA copy number at the mir17-92 locus over the normal reference probe.

Adoptive Transfer of Eli-myc HSCs

Fetal liver-derived HSCs were isolated from E13.5-E15.5 Eµ-myc/+ embryos, and were transduced with MSCV alone or MSCV expressing the mir17-19b cluster. To exclude the possibility that the observed acceleration of lymphomagenesis was due to insertional mutagenesis, experiments were carried out with individual infections for MSCV 17-19b and MSCV control using fetal liver cells isolated from 8 Eµ-myc/+ embryos. The MSCV retroviral vector used in our studies contains the PGK-puromycin-IRES-GFP (PIG) cassette[18]. Infection rates, as assessed by FACS sorting were typically 40% of bulk fetal-liver cells. HSCs infected with MSCV-mir17-19b-PIG and MSCV-PIG (control) were subsequently transplanted into 6-8 week old, lethally irradiated C57BL/6 recipient mice[17]. Tumor onset was monitored by blood smear analysis, and tumor samples were either collected into 4% paraformaldehyde for histopathological studies, or prepared as single cell suspension for FACS.

We also carried out a screen of 96 miRNAs to look for miRNA(s) that accelerate myc induced lymphomagenesis. In this experiment, each pre-miRNA with ~50 bp flanking sequence was cloned downstream of the CMV promoter in a MSCV vector containing SV40-GFP. Eight individual MSCV constructs, each overexpressing a specific miRNA, were pooled at equal concentration. 12 pools of DNA were each used to produce virus to infect Eµ-myc/+ fetal liver cells for adoptive transfer into 3 recipient animals as described above. Recipient animals were monitored for at least 6 months for tumor growth. For those that developed lymphoma, tumor cells were prepared from the enlarged lymph nodes, and then subjected to FACS analysis for GFP expression.

Histopathology

Tissue samples were fixed in 4% paraformaldehyde, embedded in paraffin, sectioned into 5 µm slices, and stained with haemotoxylin and eosin. For Ki-67 detection (rabbit anti-Ki67, NovoCastra, Newcastle, UK), representative sections were deparaffinized, rehydrated in graded alcohols, and processed using the avidin-biotin immunoperoxidase method. Sections were then subjected to antigen retrieval by microwave oven treatment, following standard procedures. Diaminobenzidine was used as the chromogen and hematoxylin as the nuclear counterstain. For B220 immunohistochemistry (rat anti-mouse CD45R/B220-clone RA3-6B2, BD Biosciences Pharmingen), and pretreatment for antigen retrieval was not required. Analysis of the apoptotic rate by TUNEL assay was performed according to a published protocol[28].

REFERENCES

1. Ota, A. et al. Identification and characterization of a novel gene, C13orf25, as a target for 13q31-q32 amplification in malignant lymphoma. *Cancer Res* 64, 3087-95 (2004).
2. Lee, Y. et al. The nuclear RNase III Drosha initiates microRNA processing. *Nature* 425, 415-9 (2003).
3. Bernstein, E., Caudy, A. A., Hammond, S. M. & Hannon, G. J. Role for a bidentate ribonuclease in the initiation step of RNA interference. *Nature* 409, 363-6 (2001).
4. Bartel, D. P. MicroRNAs: genomics, biogenesis, mechanism, and function. *Cell* 116, 281-97 (2004).
5. Ambros, V. The functions of animal microRNAs. *Nature* 431, 350-5 (2004).
6. He, L. & Hannon, G. J. MicroRNAs: small RNAs with a big role in gene regulation. *Nat Rev Genet* 5, 522-31 (2004).
7. Ruvkun, G. & Giusto, J. The *Caenorhabditis elegans* heterochronic gene lin14 encodes a nuclear protein that forms a temporal developmental switch. *Nature* 338, 313-9 (1989).
8. Ambros, V. A hierarchy of regulatory genes controls a larva-to-adult developmental switch in *C. elegans*. *Cell* 57, 49-57 (1989).
9. Chang, S., Johnston, R. J., Jr., Frokjaer-Jensen, C., Lockery, S. & Hobert, O. MicroRNAs act sequentially and asymmetrically to control chemosensory laterality in the nematode. *Nature* 430, 785-9 (2004).
10. Johnston, R. J. & Hobert, O. A microRNA controlling left/right neuronal asymmetry in *Caenorhabditis elegans*. *Nature* 426, 845-9 (2003).
11. Brennecke, J., Hipfner, D. R., Stark, A., Russell, R. B. & Cohen, S. M. bantam encodes a developmentally regulated microRNA that controls cell proliferation and regulates the proapoptotic gene hid in *Drosophila*. *Cell* 113, 25-36 (2003).
12. Chen, C. Z., Li, L., Lodish, H. F. & Bartel, D. P. MicroRNAs modulate hematopoietic lineage differentiation. *Science* 303, 83-6 (2004).
13. Knuutila, S. et al. DNA copy number amplifications in human neoplasms: review of comparative genomic hybridization studies. *Am J Pathol* 152, 1107-23 (1998).
14. Tanzer, A. & Stadler, P. F. Molecular evolution of a microRNA cluster. *J Mol Biol* 339, 327-35 (2004).
15. Tusher, V. G., Tibshirani, R. & Chu, G. Significance analysis of microarrays applied to the ionizing radiation response. *Proc Natl Acad Sci USA* 98, 5116-21 (2001).
16. Adams, J. M. et al. The c-myc oncogene driven by immunoglobulin enhancers induces lymphoid malignancy in transgenic mice. *Nature* 318, 533-8 (1985).
17. Schmitt, C. A. et al. Dissecting p53 tumor suppressor functions in vivo. *Cancer Cell* 1, 289-98 (2002).
18. Hemann, M. T. et al. An epi-allelic series of p53 hypomorphs created by stable RNAi produces distinct tumor phenotypes in vivo. *Nat Genet* 33, 396400 (2003).
19. Hemann, M. T. et al. Suppression of tumorigenesis by the p53 target PUMA. *Proc Natl Acad Sci U S A* 101, 9333-8 (2004).

20. Wendel, H. G. et al. Survival signaling by Akt and eIF4E in oncogenesis and cancer therapy. *Nature* 428, 332-7 (2004).
21. Thomson, J. M., Parker, J., Perou, C. M. & Hammond, S. M. A custom microarray platform for analysis of microRNA gene expression. *Nature method* 1, 47-53 (2004).
22. Calin, G. A. et al. Human microRNA genes are frequently located at fragile sites and genomic regions involved in cancers. *Proc Natl Acad Sci USA* 101, 2999-3004 (2004).
23. Calin, G. A. et al. MicroRNA profiling reveals distinct signatures in B cell chronic lymphocytic leukemias. *Proc Natl Acad Sci USA* 101, 11755-60 (2004).
24. Metzler, M., Wilda, M., Busch, K., Viehmann, S. & Borkhardt, A. High expression of precursor microRNA-155/BIC RNA in children with Burkitt lymphoma. *Genes Chromosomes Cancer* 39, 167-9 (2004).
25. Michael, M. Z., S M, O. C., van Holst Pellekaan, N. G., Young, G. P. & James, R. J. Reduced accumulation of specific microRNAs in colorectal neoplasia. *Mol Cancer Res* 1, 882-91 (2003).
26. Calin, G. A. et al. Frequent deletions and down-regulation of micro-RNA genes miR15 and miR16 at 13q14 in chronic lymphocytic leukemia. *Proc Natl Acad Sci USA* 99, 15524-9 (2002).
27. Mayor, C. et al. VISTA: visualizing global DNA sequence alignments of arbitrary length. *Bioinformatics* 16, 1046-7 (2000).
28. Di Cristofano, A., De Acetis, M., Koff, A., Cordon-Cardo, C. & Pandolfi, P. P. Pten and p27KIP1 cooperate in prostate cancer tumor suppression in the mouse. *Nat Genet* 27, 222-4 (2001).

TABLE 1

Phenotypic analysis of a subset of Eμ-myc/mir17-19b tumors.

| animal | GFP | immunophenotyping | cell type | Ki67 | apoptosis[a] | pathological features |
|---|---|---|---|---|---|---|
| 1 | + | B220$^+$, Thy1$^-$, IgM$^-$ CD19$^+$, CD4$^-$, CD8$^-$ | pre-B | ++(70-80%) | low | Tumor cells invaded liver and spleen, mild infiltrations observed in lung and kidney, spleen enlarged, hindlimb paralysis |
| 2 | + | B220$^+$, Thy1$^{low}$, IgM$^-$ CD19$^+$, CD4$^-$, CD8$^-$ | pre-B | ++(80-90%) | low | Tumor cells invaded liver, lung and spleen, spleen enlarged |
| 3 | + | B220$^+$, Thy1$^-$, IgM$^-$ CD19$^+$, CD4$^-$, CD8$^-$ | pre-B | ++(80-90%) | low | Tumor cells invaded liver, lung and spleen, spleen enlarged |
| 4 | + | B220$^+$, Thy1$^{low}$, IgM$^-$ CD19$^+$, CD4$^-$, CD8$^-$ | pre-B | ++(70-80%) | low | Tumor cells invaded liver and spleen, spleen enlarged |
| 5 | + | B220$^+$, Thy1$^-$, IgM$^-$ CD19$^+$, CD4$^-$, CD8$^-$ | pre-B | ++(80-90%) | Slightly less than the control | Highly disseminated lymphoma, tumor cells invaded into liver, spleen, lung and kidney, spleen enlarged |
| 6 | + | B220$^+$, Thy1$^-$, IgM$^-$ CD19$^+$, CD4$^-$, CD8$^-$ | pre-B | ++(80-90%) | low | Highly disseminated lymphoma, tumor cells invaded liver, spleen, lung and kidney, spleen enlarged |
| 7 | + | B220$^+$, Thy1$^-$, IgM$^-$ CD19$^+$, CD4$^-$, CD8$^-$ | pre-B | ++(70-80%) | low | Spleen enlarged, mild infiltration of the tumor cells into liver only |
| 8 | + | B220$^+$, Thy1$^{low}$, IgM$^-$, CD19$^+$, CD4$^-$, CD8$^-$ and B220$^+$, Thy1$^{low}$, Igm$^-$, CD19$^+$, CD4$^-$, CD8$^{-b}$ | Pre-B and mature B | ++(70-80%) | low | Highly disseminated lymphoma, tumor cells invaded liver, |

TABLE 1-continued

Phenotypic analysis of a subset of Eµ-myc/mir17-19b tumors.

| animal | GFP | immunophenotyping | cell type | Ki67 | apoptosis[a] | pathological features |
|---|---|---|---|---|---|---|
| 9 | – | N/D | N/D | ++(80-90%) | low | spleen, lung and kidney, enlarged spleen Tumor cells invaded liver, lung and spleen, enlarged spleen |

[a] The levels of apoptosis in Eµ-myc/mir17-19blymphomas are compared to control Eµ-myc/MSCV lymphomas based on H&E staining and TUNEL staining.
[b] The two clones of tumor cells with different cell type specificity may reflect independent transformation events or maturation of a single primary clone.

TABLE 2

Significance Analysis of Microarray (SAM) analysis of 13q31 amplicon cell lines. The normalized, collapsed data set from FIG. 4 was used for SAM analysis using 2-fold minimum change restriction. Data was divided into two classes based on published presence of the amplicon as follows: Karpas 1618, OCI-Ly4, OCI-Ly7, OCI-Ly8 positive; Namalwa, HG1125, Jurkat, Manca, Raji, Negative. Six positive significant genes and zero negative significant genes were identified using a delta value of 0.202. The false discovery rate was 17%.

Significant Genes List

| Input Parameters | |
|---|---|
| Imputation Engine | 10-Nearest Neighbor Imputer |
| Data Type | Two Class, unpaired data |
| Data in log scale? | TRUE |
| Number of Permutations | 100 |
| Blocked Permutation? | FALSE |
| RNG Seed | 1234567 |
| (Delta, Fold Change) | (0.20243, 2.00000) |
| (Upper Cutoff, Lower Cutoff) | (1.65693, 4) |
| Computed Quantities | |
| Computed Exchangeability Factor S0 | 0.085654726 |
| S0 percentile | 0 |
| False Significant Number (Median, 90 percentile) | (1.00000, 4.20000) |
| False Discovery Rate (Median, 90 percentile) | (16.66667, 70.00000) |
| Pi0Hat | 1 |

6 Positive Significant Genes

| Gene Name | Score(d) | Numerator (r) | Denominator (s + s0) | Fold Change | q-value (%) |
|---|---|---|---|---|---|
| hsa-miR-92 | 2.181254144 | 1.124125 | 0.515357187 | 2.34459 | 16.66666667 |
| hsa-miR-19a | 1.990500557 | 1.06695 | 0.53602095 | 2.12908 | 16.66666667 |
| hsa-miR-20 | 1.925478851 | 1.304075 | 0.677273084 | 2.54907 | 16.66666667 |
| hsa-miR-19b | 1.887537933 | 1.33365 | 0.706555337 | 2.55144 | 16.66666667 |
| hsa-miR-17-5p | 1.729572125 | 1.126225 | 0.651158159 | 2.06056 | 16.66666667 |
| hsa-miR-106a | 1.656932745 | 1.2342 | 0.744870306 | 2.29774 | 16.66666667 |

TABLE 3

Single miRNAs overexpressed in Eµ-myc/+ HSCs.

| Pool # | miRNA subset[a] | # of recipient animals | # of animals developed lymphoma by 6 months | # of GFP positive tumors[b] |
|---|---|---|---|---|
| 1 | mmu-mir-206 mmu-mir-30a mmu-mir-30c-2 mmu-mir-26b | 3 | 3 | 0 |
| | mmu-mir-135b mmu-mir-213 mmu-mir-199a-2 mmu-mir-350 | | | |

TABLE 3-continued

Single miRNAs overexpressed in Eμ-myc/+ HSCs.

| Pool # | miRNA subset[a] | # of recipient animals | # of animals developed lymphoma by 6 months | # of GFP positive tumors[b] |
|---|---|---|---|---|
| 2 | mmu-mir-205<br>mmu-mir-129-2<br>mmu-mir-350<br>mmu-mir-126<br>mmu-mir-219-2<br>mmu-mir-130a<br>mmu-mir129-2<br>mmu-mir 103-2 | 3 | 1 | 0 |
| 3 | mmu-mir-296<br>mmu-mir-124a-2<br>mmu-mir-15b<br>mmu-mir-16-2<br>mmu-mir-302<br>mmu-mir-186<br>mmu-mir-32<br>mmu-mir-31 | 3 | 2 | 0 |
| 4 | mmu-mir-101<br>mmu-mir-30c-1<br>mmu-mir-30e<br>mmu-mir-200a<br>mmu-mir-200b<br>mmu-mir-25<br>mmu-mir-93<br>mmu-mir-106b | 3 | 3 | 0 |
| 5 | mmu-mir-339<br>mmu-mir-129-1<br>mmu-mir-96<br>mmu-mir-183<br>mmu-mir-29a<br>mmu-mir-141<br>mmu-mir-200c<br>mmu-mir-290 | 3 | 1 | 0 |
| 6 | mmu-mir-291<br>mmu-mir-292<br>mmu-mir-293<br>mmu-mir-295<br>mmu-mir-330<br>mmu-mir-150<br>mmu-mir-344<br>mmu-mir-211 | 3 | 1 | 0 |
| 7 | mmu-mir-7-2<br>mmu-mir-9-3<br>mmu-mir-326<br>mmu-mir-181c<br>mmu-mir-23a<br>mmu-mir-27a<br>mmu-mir-24-2<br>mmu-mir-328 | 3 | 2 | 0 |
| 8 | mmu-mir-140<br>mmu-mir-10a-2<br>mmu-mir-100<br>mmu-let-7a-2<br>mmu-mir-125b-1<br>mmu-mir-34c<br>mmu-mir-34b<br>mmu-mir-190 | 3 | 2 | 0 |
| 9 | mmu-mir-184<br>mmu-let-7g<br>mmu-mir-191<br>mmu-mir-26a-1<br>mmu-mir-331<br>mmu-let-7i<br>mmu-mir-26a-2<br>mmu-mir-216 | 3 | 2 | 0 |
| 10 | mmu-mir-217<br>mmu-mir-103-1<br>mmu-mir-340<br>mmu-mir-324<br>mmu-mir-195<br>mmu-mir-132<br>mmu-mir-22<br>mmu-mir-144 | 3 | 1 | 0 |
| 11 | mmu-mir-193<br>mmu-mir-301<br>mmu-mir-142<br>mmu-mir-10a-2<br>mmu-mir-338<br>mmu-mir-342<br>mmu-mir-345<br>mmu-mir-337 | 3 | 1 | 0 |
| 12 | mmu-mir-136<br>mmu-mir-329<br>hsa-mir-200b<br>hsa-mir-200a<br>hsa-mir-30c-1<br>hsa-mir-197<br>hsa-mir-214<br>has-mir-199a-2 | 3 | 0 | 0 |

[a] 8 individual MSCV constructs, each overexpressing a specific miRNA, were pooled at equal DNA concentration. The pooled DNA was used to produce virus to infect Eμ-myc/+ fetal liver cells for adoptive transfer.
[b] Recipient animals were monitored for at least 6 months for tumor growth. For those that developed lymphomas, tumor cells were prepared from the enlarged lymph nodes, and then subjected to FACS analysis for GFP expression. The GFP expression is an indication that the tumors are derived from transduced Eμ-myc/+ fetal liver cells.

What is claimed is:

1. A method for decreasing the expression or activity of miR-19b in a cell from a B-cell malignancy, comprising contacting a cell from a B-cell malignancy with a nucleic acid compound that hybridizes to miR-19b, wherein the nucleic acid compound decreases the expression or activity of miR-19b, and wherein the nucleic acid compound is an antisense nucleic acid.

2. The method of claim 1, wherein the nucleic acid compound comprises one or more modified backbone or base moieties.

3. The method of claim 2, wherein the nucleic acid compound is resistant to endogenous nucleases.

4. The method of claim 2, wherein the nucleic acid compound is stable in vivo.

5. The method of claim 1, wherein the B-cell malignancy is a myc-induced B-cell malignancy.

6. The method of claim 1, wherein the cell from the B-cell malignancy is a mouse cell.

7. The method of claim 1, wherein the cell from the B-cell malignancy is a human cell.

8. The method of claim 1, wherein the cell from the B-cell malignancy is in vitro.

9. The method of claim 1, wherein the nucleic acid compound comprises SEQ ID NO: 11.

10. The method of claim 1, further comprising contacting the cell from the B-cell malignancy with an antisense nucleic acid that hybridizes to miR-18.

11. The method of claim 1, further comprising contacting the cell from the B-cell malignancy with a chemotherapeutic agent.

12. The method of claim 1, further comprising contacting the cell from the B-cell malignancy with an anti-CD20 monoclonal antibody or an anti-CD22 antibody.

13. A method for decreasing the expression or activity of miR-18 in a cell from a B-cell malignancy, comprising contacting a cell from a B-cell malignancy with a nucleic acid compound that hybridizes to miR-18 wherein the nucleic acid compound decreases the expression or activity of miR-18, and wherein the nucleic acid compound is an antisense nucleic acid.

14. The method of claim 13, wherein the nucleic acid compound comprises one or more modified backbone or base moieties.

15. The method of claim 14, wherein the nucleic acid compound is resistant to endogenous nucleases.

16. The method of claim 14, wherein the nucleic acid compound is stable in vivo.

17. The method of claim 13, wherein the B-cell malignancy is a myc-induced B-cell malignancy.

18. The method of claim 13, wherein the cell from the B-cell malignancy is a mouse cell.

19. The method of claim 13, wherein the cell from the B-cell malignancy is a human cell.

20. The method of claim 13, wherein the cell from the B-cell malignancy is in vitro.

21. The method of claim 13, wherein the nucleic acid compound comprises SEQ ID NO: 12.

22. The method of claim 13, further comprising contacting the cell from the B-cell malignancy with an antisense nucleic acid that hybridizes to mir-19b.

23. The method of claim 13, further comprising contacting the cell from the B-cell malignancy with a chemotherapeutic agent.

24. The method of claim 13, further comprising contacting the cell from the B-cell malignancy with an anti-CD20 monoclonal antibody or an anti-CD22 antibody.

* * * * *